US010227610B2

(12) United States Patent
Chen et al.

(10) Patent No.: US 10,227,610 B2
(45) Date of Patent: Mar. 12, 2019

(54) METHODS AND COMPOSITIONS FOR ENHANCING NUCLEASE-MEDIATED GENE DISRUPTION

(71) Applicants: SANGAMO THERAPEUTICS, INC., Richmond, CA (US); SIGMA ALDRICH CO. LLC, Saint Louis, MO (US)

(72) Inventors: Fuqiang Chen, St. Louis, MO (US); Qiaohua Kang, Saint Louis, MO (US); Thomas Wechsler, Richmond, CA (US)

(73) Assignees: Sangamo Therapeutics, Inc., Richmond, CA (US); Sigma Aldrich Co LLC, St. Louis, MO (US)

(*) Notice: Subject to any disclaimer, the term of this patent is extended or adjusted under 35 U.S.C. 154(b) by 0 days.

(21) Appl. No.: 14/188,212

(22) Filed: Feb. 24, 2014

(65) Prior Publication Data
US 2014/0242702 A1 Aug. 28, 2014

Related U.S. Application Data

(60) Provisional application No. 61/769,038, filed on Feb. 25, 2013.

(51) Int. Cl.
*C12N 9/22* (2006.01)
*C12N 15/90* (2006.01)
*A61K 31/502* (2006.01)
*A61K 31/5377* (2006.01)

(52) U.S. Cl.
CPC .......... *C12N 15/907* (2013.01); *A61K 31/502* (2013.01); *A61K 31/5377* (2013.01); *C12N 9/22* (2013.01); *C07K 2319/80* (2013.01); *C07K 2319/81* (2013.01)

(58) Field of Classification Search
None
See application file for complete search history.

(56) References Cited

U.S. PATENT DOCUMENTS

| | | |
|---|---|---|
| 5,789,538 A | 8/1998 | Rebar et al. |
| 5,925,523 A | 7/1999 | Dove et al. |
| 6,007,988 A | 12/1999 | Choo |
| 6,013,453 A | 1/2000 | Choo |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,794,136 B1 | 9/2004 | Eisenberg et al. |
| 6,824,978 B1 | 11/2004 | Cox, III et al. |
| 6,903,185 B2 | 6/2005 | Kim et al. |
| 6,933,113 B2 | 8/2005 | Case et al. |
| 6,974,867 B2 | 12/2005 | Wu et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,074,596 B2 | 7/2006 | Darzynkiewicz et al. |
| 7,153,949 B2 | 12/2006 | Kim et al. |
| 7,163,824 B2 | 1/2007 | Cox, III et al. |
| 7,253,273 B2 | 8/2007 | Collingwood |
| 7,262,054 B2 | 8/2007 | Jamieson et al. |
| 7,361,635 B2 | 4/2008 | Miller et al. |
| 7,888,121 B2 | 2/2011 | Urnov et al. |
| 7,914,796 B2 | 3/2011 | Miller et al. |
| 7,919,313 B2 | 4/2011 | Collingwood et al. |
| 7,951,925 B2 | 5/2011 | Ando et al. |
| 8,034,598 B2 | 10/2011 | Miller |
| 8,071,579 B2* | 12/2011 | Ashworth ............ A61K 31/00 514/183 |
| 8,110,379 B2 | 2/2012 | DeKelver et al. |
| 8,153,399 B2 | 4/2012 | Liu et al. |
| 8,153,773 B2 | 4/2012 | Jemielity et al. |
| 8,399,218 B2 | 3/2013 | Gupta et al. |
| 8,409,861 B2 | 4/2013 | Guschin et al. |
| 8,420,782 B2 | 4/2013 | Bonas et al. |
| 8,440,431 B2 | 5/2013 | Voytas et al. |
| 8,586,526 B2 | 11/2013 | Gregory et al. |

(Continued)

FOREIGN PATENT DOCUMENTS

| | | |
|---|---|---|
| GB | 2338237 A | 12/1999 |
| WO | WO 95/19431 A1 | 7/1995 |

(Continued)

OTHER PUBLICATIONS

Wang M et al. PARP-1 and Ku compete for repair for DNA double strand breaks by distinct NHEJ pathways. 2006. Nucleic Acids Research. vol. 34, No. 21. 6170-6182.*

Kim TK et al. Mammalian cell transfection: the present and the future. Analytical and Bioanalytical Chemistry. 397:3173-3178. (Year : 2010).*

Beerli, et al., "Engineering Polydactyl Zinc-Finger Transcription Factors," *Nature Biotechnol.* 20:135-141(2002).

Beurdeley, et al., "Compact Designer Talens for Efficient Genome Engineering," *Nature Communications* 4:1762 (2013) doi:10.10.38/ncomms2782.

(Continued)

*Primary Examiner* — Paul J Holland

(74) *Attorney, Agent, or Firm* — Pasternak Patent Law; Susan Abrahamson

(57) ABSTRACT

Methods and compositions for increasing nuclease-mediated genomic modification using DNA repair inhibitors are provided.

8 Claims, 12 Drawing Sheets

(56) References Cited

U.S. PATENT DOCUMENTS

| | | | |
|---|---|---|---|
| 8,597,912 | B2 | 12/2013 | Collingwood et al. |
| 8,623,618 | B2 | 1/2014 | Doyon et al. |
| 2003/0232410 | A1 | 12/2003 | Liljedahl et al. |
| 2005/0026157 | A1 | 2/2005 | Baltimore et al. |
| 2005/0064474 | A1 | 3/2005 | Urnov et al. |
| 2005/0208489 | A1 | 9/2005 | Carroll et al. |
| 2005/0227919 | A1 | 10/2005 | Ashworth et al. |
| 2005/0267061 | A1 | 12/2005 | Martin |
| 2006/0063231 | A1 | 3/2006 | Li et al. |
| 2006/0188987 | A1 | 8/2006 | Guschin et al. |
| 2007/0117128 | A1* | 5/2007 | Smith .............. C12N 9/22 435/6.12 |
| 2007/0218528 | A1 | 9/2007 | Miller |
| 2008/0131962 | A1 | 6/2008 | Miller |
| 2008/0159996 | A1 | 7/2008 | Ando et al. |
| 2009/0117617 | A1 | 5/2009 | Holmes et al. |
| 2009/0203140 | A1 | 8/2009 | Amacher et al. |
| 2010/0003756 | A1 | 1/2010 | Collingwood et al. |
| 2010/0047805 | A1 | 2/2010 | Wang |
| 2010/0218264 | A1 | 8/2010 | Cui et al. |
| 2010/0291048 | A1 | 11/2010 | Holmes et al. |
| 2011/0041195 | A1 | 2/2011 | Freudenberger et al. |
| 2011/0201055 | A1 | 8/2011 | Doyon et al. |
| 2011/0207221 | A1 | 8/2011 | Cost et al. |
| 2011/0265198 | A1 | 10/2011 | Gregory et al. |
| 2011/0281361 | A1 | 11/2011 | DeKelver et al. |
| 2012/0017290 | A1 | 1/2012 | Cui et al. |
| 2012/0244131 | A1 | 1/2012 | Delacote et al. |
| 2013/0122591 | A1 | 5/2013 | Cost et al. |
| 2013/0137104 | A1 | 5/2013 | Cost et al. |
| 2013/0177960 | A1 | 7/2013 | Rebar |
| 2013/0177983 | A1 | 7/2013 | Rebar |
| 2014/0017212 | A1 | 1/2014 | Rebar |
| 2014/0080216 | A1 | 3/2014 | Cost et al. |
| 2014/0093913 | A1 | 4/2014 | Cost et al. |
| 2015/0056705 | A1 | 2/2015 | Conway et al. |

FOREIGN PATENT DOCUMENTS

| | | | | |
|---|---|---|---|---|
| WO | WO 96/06166 | A1 | 2/1996 | |
| WO | WO 98/37186 | A1 | 8/1998 | |
| WO | WO 98/53057 | A1 | 11/1998 | |
| WO | WO 98/53058 | A1 | 11/1998 | |
| WO | WO 98/53059 | A1 | 11/1998 | |
| WO | WO 98/53060 | A1 | 11/1998 | |
| WO | WO 98/54311 | A1 | 12/1998 | |
| WO | WO 00/27878 | A1 | 5/2000 | |
| WO | WO 01/60970 | A2 | 8/2001 | |
| WO | WO 01/88197 | A2 | 11/2001 | |
| WO | WO 02/016536 | A1 | 2/2002 | |
| WO | WO 02/077227 | A2 | 10/2002 | |
| WO | WO 02/099084 | A2 | 12/2002 | |
| WO | WO 03/016496 | A2 | 2/2003 | |
| WO | 2007013979 | A2 | 2/2007 | |
| WO | WO 07/014275 | A2 | 2/2007 | |
| WO | WO 2007013979 | A2 * | 2/2007 | ........... C12N 15/113 |
| WO | WO 10/079430 | A1 | 7/2010 | |
| WO | WO 12/168307 | A2 | 12/2012 | |
| WO | 2014127287 | A1 | 8/2014 | |

OTHER PUBLICATIONS

Boch, et al., "Breaking the Code of DNA Binding Specificity of Tal-Type III Effectors," *Science* 326:1509-1512 (2009).

Boissel, et al., "Megatals: A Rare-Cleaving Nuclease Architecture for Therapeutic Genome Engineering," *Nucl. Acid. Res.* 1-11 (2013) doi:10.1093/nar/gkt1224.

Boissel, et al., "Megatals: A Rare-Cleaving Nuclease Architecture for Therapeutic Genome Engineering," *Nucl. Acid. Res.* 42(4):2591-2601(2014) doi:10.1093/nar/gkt1224 (epub 2014).

Bonas, et al., "Genetic and Structural Characterization of the Avirulence Gene AVRBS3 From Xanthomonas Campestris PV. Vesicatoria," *Mol. Gen. Genet.* 218:127-136 (1989).

Ceccia and Elledge, "The DNA Damage Response: Making It Safe to Play With Knives," *Mol. Cell.* 40(2):179-204 (2010).

Choo, et al., "Advances in Zinc Finger Engineering," *Curr. Opin. Struct. Biol.* 10:411-416 (2000).

Haft, et al., "A Guild of 45 CRISPR-Associated (CAS) Protein Families and Multiple CRISPR/CAS Subtypes Exist in Prokaryotic Genomes," *PLoS Comput. Biol.* 1(6):474-483 (2005).

Heuer, et al., "Repeat Domain Diversity of AVRBS3-Like Genes in Ralstonia Solanacearum Strains and Association With Host Preferences in the Field," *Appl. and Envir. Micro.* 73(13):4379-4384 (2007).

Isalan, et al., "A Rapid, Generally Applicable Method to Engineer Zinc Fingers Illustrated by Targeting the HIV-1 Promoter," *Nat. Biotechnol.* 19:656-660 (2001).

Jia, et al., Agrobacterium Tumefaciens T-DNA Integration and Gene Targeting in *Arabidopsis thaliana* Non-Homologous End-Joiningmutants, *J. Botany* 2012:13 pages (2012) doi: 10.1155/2012/989272.

Jansen, et al., "Identification of Genes That Are Associated With DNA Repeats in Prokaryotes," *Molecular Microbiology* 43(6):1565-1575 (2002).

Jinek, et al., "A Programmable Dual-RNA-Guided DNA Endonuclease in Adaptive Bacterial Immunity," *Science* 337:816-821 (2012).

Kay, et al., "A Bacterial Effector Acts As a Plant Transcription Factor and Induces a Cell Size Regulator," *Science* 318:648-651 (2007).

Makarova, et al., "A DNA Repair System Specific for Thermophilic Archaea and Bacteria Predicted by Genomic Context Analysis," *Nucleic Acids Res.* 30:482-496 (2002).

Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biol. Direct* 1:7 (2006).

Moscou, et al., "A Simple Cipher Governs DNA Recognition by TAL Effectors," *Science* 326:1501 (2009).

O'Connor, et al., "Targeted Cancer Therapies Based on the Inhibition of DNA Strand Break Repair," *Oncogene* 26(56):7816-7824 (2007).

Pabo, et al., "Design and Selection of Novel CYS2HIS2 Zinc Finger Proteins," *Ann. Rev. Biochem.* 70:313-340 (2001).

Puchta, "The Repair of Double-Strand Breaks in Plants: Mechanisms and Consequences for Genome Evolution," *J. Exp. Bio.* 56(409):1-14 (2005).

Schornack, et al., "Gene-For-Gene-Mediated Recognition of Nuclear-Targeted AVRBS3-Like Bacterial Effector Proteins," *J. Plant Physiol.* 163(3):256-272 (2006).

Segal, et al., "Custom DNA-Binding Proteins Come of Age: Polydactyl Zinc-Finger Proteins," *Curr. Opin. Biotechnol.* 12:632-637 (2001).

Urnov, et al., "Genome Editing With Engineered Zinc Finger Nucleases," *Nat. Rev. Genet.* 11(9):636-646 (2010).

Wang, et al., "PARP-1 and KU Compete for Repair of DNA Double Strand Breaks by Distinct NHEJ Pathways," *Nucleic Acids Research* 34(21):6170-6182 (2006).

Cong, et al., "Multiplex Genome Engineering Using CRISPR/CAS Systems," Science 339:819-823 (2013).

Narsinh, et al., "Gene Correction in Human Embryonic and Induced Pluripotent Stem Cells: Promises and Challenges Ahead," Molecular Therapy 18(6):1061-1063 (2010).

Cong, et al., "Gene Correction in Human Embryonic and Induced Pluripotent Stem Cells: Promises and Challenges Ahead," Molecular Therapy 18(6):1061-1063 (2010).

Narsinh, et al., "Multiplex Genome Engineering Using CRISPR/CAS Systems" Science 339(6121):819-823 (2015).

Imai, et al., "Comparing Antibody and Small-Molecule Therapies for Cancer, " Nature Reviews Cancer 6(9):714-727 (2006).

Ishida, et al., "Discovery of Potent and Selective PARP-1 and PARP-2 Inhibitors: SBDD Analysis Via a Combination of X-Ray Structural Study and Homology Modeling," Bioorganic & Medicinal Chemistry 14(5):1378-1390 (2006).

Tavecchio, et al., "Further Characterisation of the Cellular Activity of the DNA-PK Inhibitor, NU7441, Reveals Potential Cross-Talk With Homologous Recombination," Cancer Chemotherapy & Pharmacology 69(1):155-164 (2011).

(56) References Cited

OTHER PUBLICATIONS

Franco, et al. "Accessibility of chromosomal recombination breaks in nuclei of wild-type and DNA-PKcs-deficient cells," DNA Repair 8(7): 813-821 (2009).

Mladenov, et al. "Induction and repair of DNA double strand breaks: the increasing spectrum of non-homologous end joining pathways," Mutation Research 711(1): 61-72 (2011).

Mitchell, et al., "Poly(ADP-Ribose) Polymerase-1 and DNA-Dependent Protein Kinase Have Equivalent Roles in Double Strand Break Repair Following Ionizing Radiation, " International Journal of Radiation Oncology 75(5): 1520-1527 (2009).

Morozov, et al., "Single-strand DNA-mediated targeted mutagenesis of genomic DNA in early mouse embryos is stimulated by Rad51/54 and by Ku70/86 inhibition," Gene Therapy 15(6):468-472 (2008).

Dolan, et al., "Systems modelling of NHEJ reveals the importance of redox regulation of Ku70/80 in the dynamics of dna damage foci," PLos One 8(2): e55190 (2014).

McVey, et al., "MMEJ repair of double-strand breaks (director's cut): deleted sequences and alternative endings," Trends in Genetics 24(11): 529-538 (2008).

Perrault, et al., "Backup pathways of NHEJ are suppressed by DNA-PK," J. of Cellular Biochemistry 92(4): 781-794 (2004).

\* cited by examiner

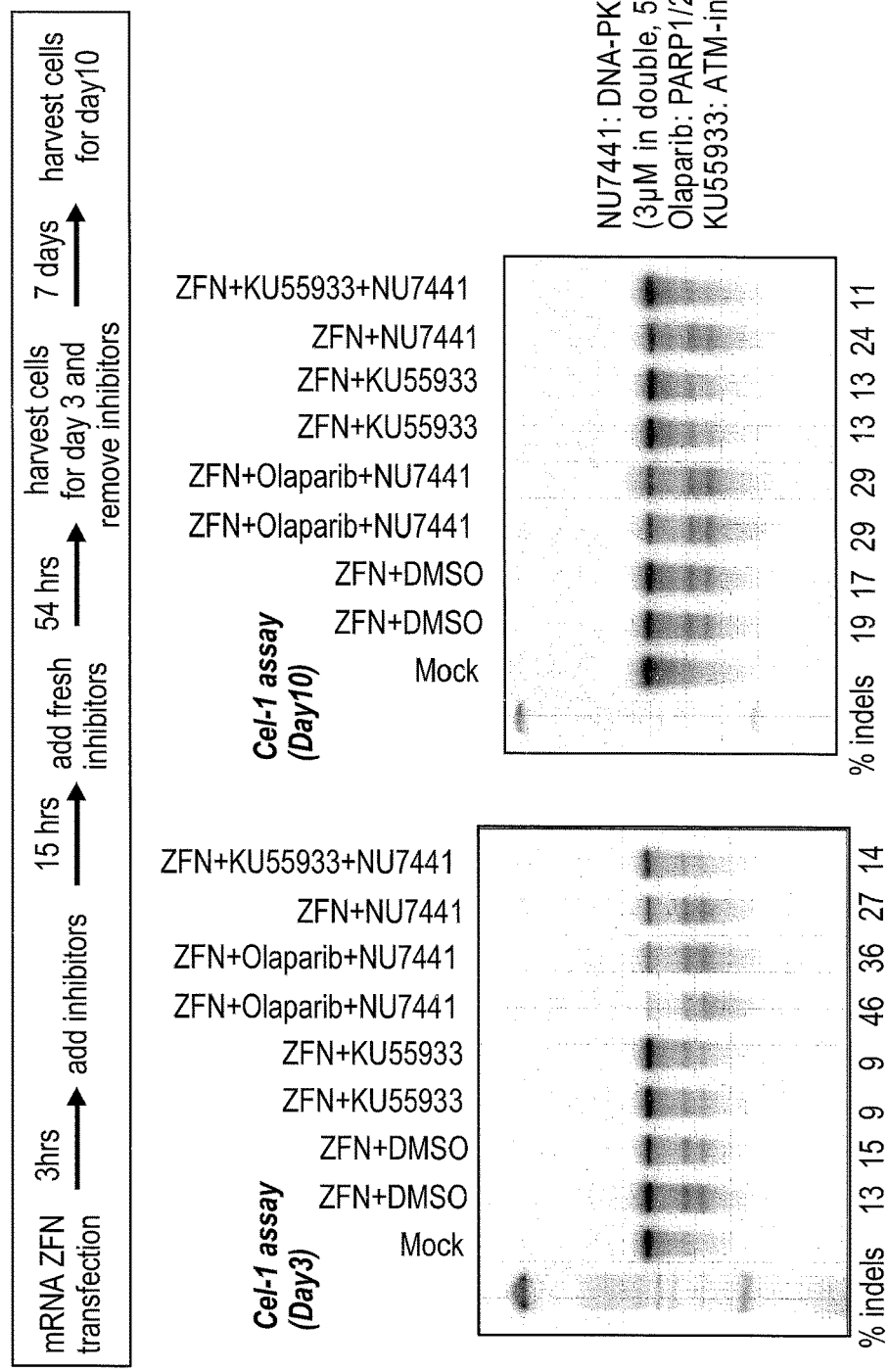

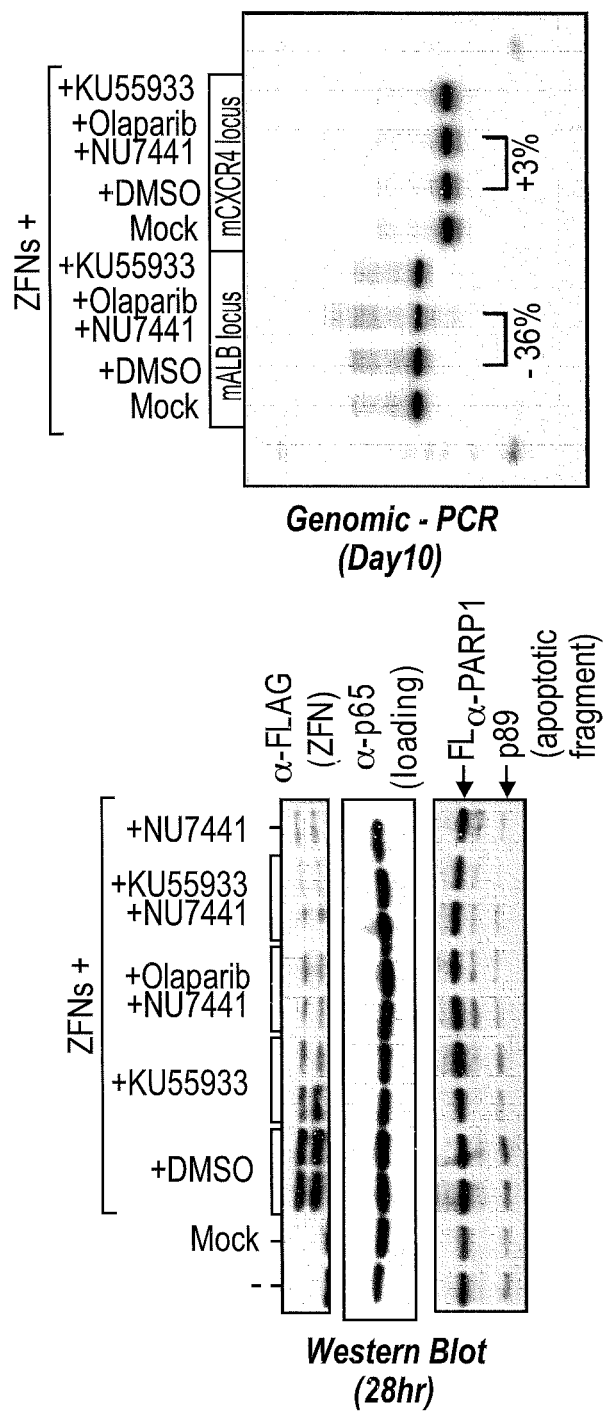

| Target | Inhibitor | Day3 | Day10 |
|---|---|---|---|
| - | - | 0.3 | 0.3 |
| DNA-PKcs | NU7441 | n.d. | 1.3 |
| DNA-PKcs+ PARP (1/2) | NU7441+ Olaparib | 2.6 | 2.1 |
| ATM | KU55993 | 0.03 | 0.02 | by miSEQ analysis
(13216-38981 sequences)

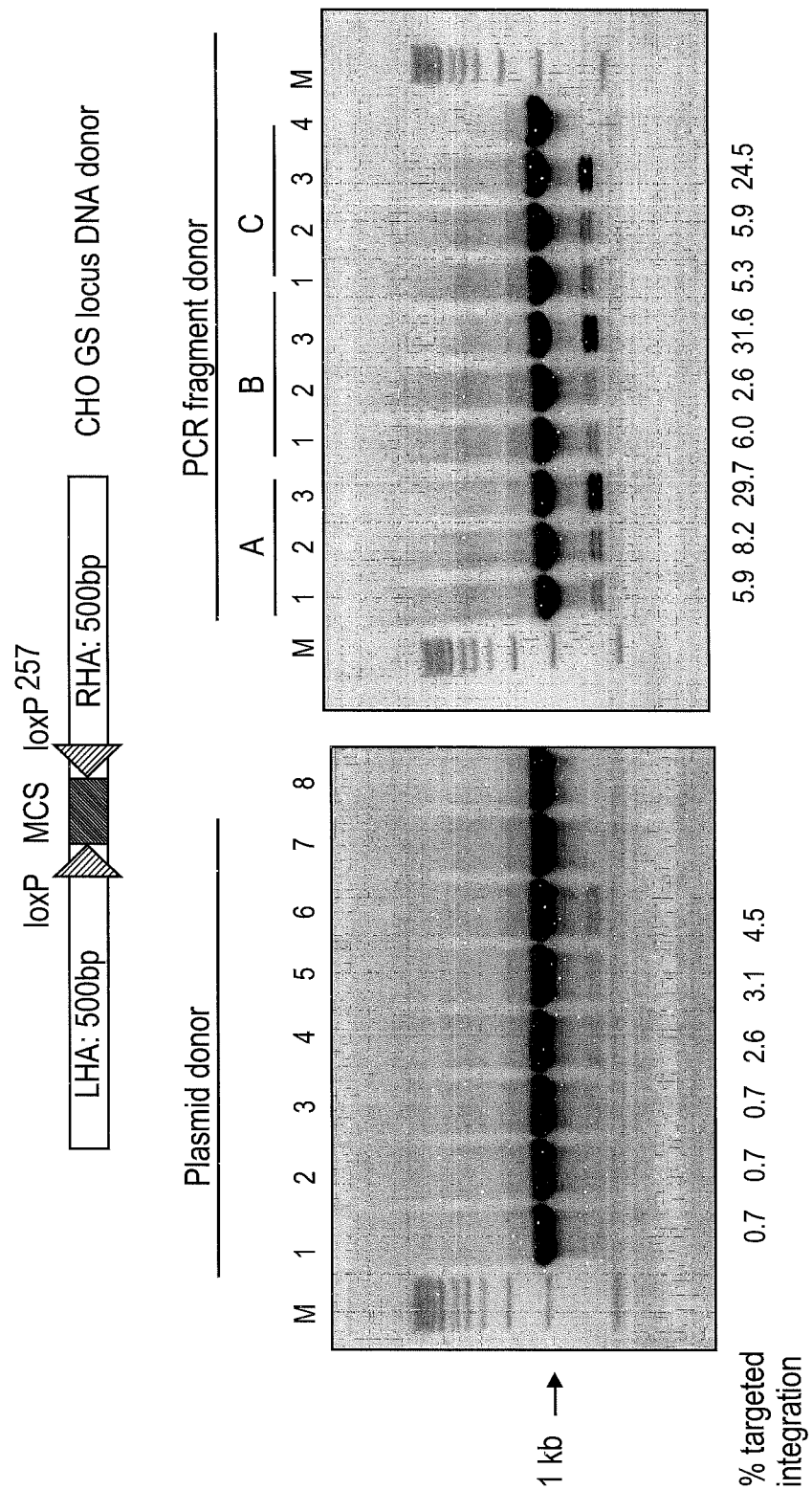

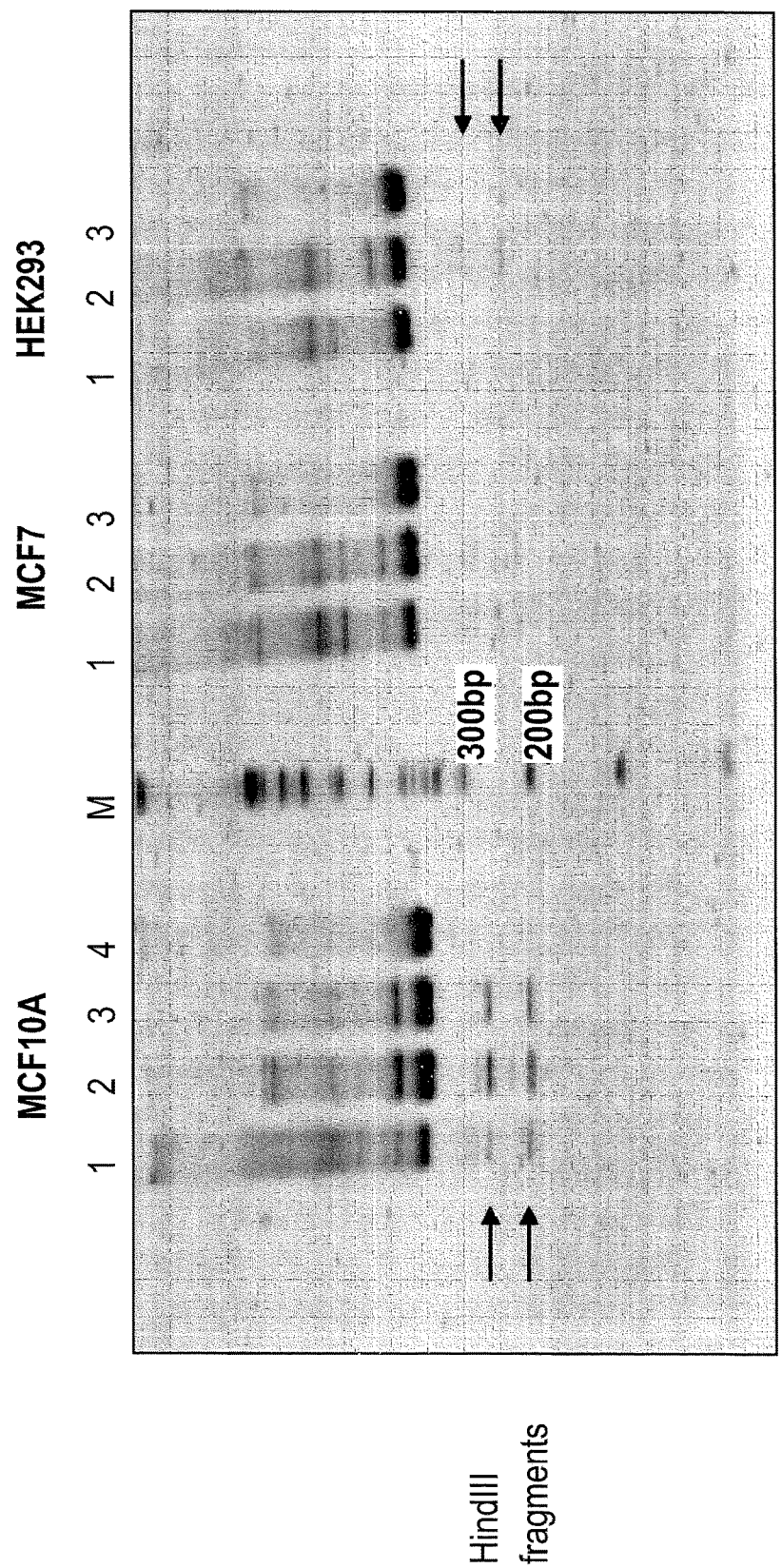

METHODS AND COMPOSITIONS FOR ENHANCING NUCLEASE-MEDIATED GENE DISRUPTION

CROSS-REFERENCE TO RELATED APPLICATIONS

The present application claims the benefit of U.S. Provisional Application No. 61/769,038, filed Feb. 25, 2013, the disclosure of which is hereby incorporated by reference in its entirety.

TECHNICAL FIELD

The present disclosure is in the fields of genome editing and therapeutics.

BACKGROUND

Engineered nucleases, including zinc finger nucleases, TALENs, CRISPR/Cas nuclease systems, and homing endonucleases designed to specifically bind to target DNA sites are useful in genome engineering. For example, zinc finger nucleases (ZFNs) and TALENs (including TALENs comprising Fok1-TALE DNA binding domain fusions, Mega TALs and compact TALENs) are proteins comprising engineered site-specific zinc fingers or TAL-effector domains fused to a nuclease domain ZFNs and TALENs have been successfully used for genome modification in a variety of different species. See, for example, U.S. Pat. Nos. 7,888,121; 8,409,861; 8,586,526; 7,951,925; 8,110,379; 7,919,313; 8,597,912; 8,153,399; 8,399,218; and United States Patent Publications 20090203140; 20100291048; 20100218264; and 20110041195, the disclosures of which are incorporated by reference in their entireties for all purposes. Additionally, the CRISPR/Cas system can be manipulated through use of an engineered crRNA/tracr RNA ('single guide RNA') to perform genome engineering (Jinek et al. (2012) *Science* 337 p 816-821). See, for example, U.S. Publication No. 20150056705.

These engineered nucleases and engineered nuclease systems can create a double strand break (DSB) in a target nucleotide sequence, which increases the frequency of homologous recombination at the targeted locus by more than 1000-fold. In addition, the inaccurate repair of a site-specific DSB by non-homologous end joining (NHEJ) and other pathways can also result in gene disruption.

In mammalian and plant cells these DNA lesions are repaired by an extensive array of well-characterized DNA-repair pathways. See, e.g., Ciccia and Elledge (2010) *Mol. Cell.* 40(2):179-204 and Puchta (2005) *J Exp Bio* 56(409): 1-14. The choice of these pathways depends both on the DNA lesion type and on the status of the cell cycle with a preference for non-homologous end joining (NHEJ) in G1 phase and homology-directed repair (HDR) during or after S-phase. But even for a defined lesion in a defined cell cycle status, the cell can choose from a variety of molecular tools for repair. These pathways are thought to follow a hierarchy which first prefers error-free pathways and secondary, as a last resort, error-prone pathways.

For the use of nucleases such as ZFNs and TALENs or nuclease systems such as CRIPSR/Cas, in gene therapy or genome engineering, the desired repair outcome at the site of the cleavage is either gene disruption (e.g., inactivation) or gene correction. See, e.g., Urnov et al. (2010) *Nat Rev Genet.* 11(9):636-46. The vast majority of the 5' four base overhangs that are generated by artificial nucleases comprising Fok1 cleavage domains in vivo and in vitro are repaired error-free by classic DNA-PKcs dependent NHEJ (also termed "C-NHEJ") rather than by the more error-prone alternative NHEJ ("A-NHEJ"). It has been shown that A-NHEJ can be carried out by a complex including Poly-(ADP-ribose) polymerase 1 (PARP1), an enzyme which also contributes to single strand break (SSB) repair. Alternatively, DSBs can also be repaired by other, even more error-prone pathways like microhomology-mediated end joining (MMEJ) which is known to use small DNA sequence homologies and DNA end-resection at the site of damage (shown in FIG. 1). DSB repair pathways follow a hierarchy of activation from error-free to error-prone repair, so in order to achieve error-prone repair, the error-free pathway must first be inhibited.

Mammalian and plant cells can also use HDR if a DNA repair template is available. This repair template can either be a homologous chromosome, a sister chromatid or, in the case of gene therapy, a transfected single or double-stranded DNA donor template with any gene sequence (e.g., transgene) as long as the donor contains regions of homology with the targeted sequence. In order to achieve gene correction via HDR the cells must either be in S-phase where HDR is preferred over NHEJ or the cell must exhaust all its NHEJ-like repair options before resorting to HDR. Another possible scenario for HDR induction is the persistence of DNA damage inflicted during G1 until S-phase. If there are persistent SSBs and DSBs that are encountered by DNA replication forks during DNA replication, the replication forks can collapse, form DSBs which, subsequently, are repaired by HDR directed repair.

Thus, there remains a need for methods and compositions that shift nuclease-mediated error-free DNA repair to both error-prone and HDR-mediated DNA repair events to enhance nuclease-mediated gene disruption and targeted integration.

SUMMARY

The present disclosure relates to methods and compositions for inhibiting repair via classic and alternative NHEJ mechanisms in cells to increase gene disruption mediated by a nuclease (e.g., ZFN or TALEN) or nuclease system (e.g. CRISPR/Cas). By inhibiting the critical enzymatic activities of these NHEJ DNA repair pathways, for example using small molecule inhibitors of DNA-dependent-protein kinase catalytic subunit (DNA-PKcs) and/or Poly-(ADP-ribose) polymerase 1/2 (PARP1/2), the level of gene disruption by nucleases is increased by forcing cells to resort to more error prone repair pathways than classic NHEJ, such as alternate NHEJ and/or microhomology mediated end-joining. In addition, inhibition of the NHEJ pathways also increases efficiency of HDR targeted integration in the presence of a suitable donor or repair template. Thus, the methods and compositions described herein significantly increase the efficiency of nuclease-mediated gene disruption and nuclease-mediated targeted gene integration in a host cell.

In one aspect, described herein is a method for increasing gene disruption (e.g., deletions and/or additions) of an exogenous nuclease in a cell by subjecting the cell to conditions that inhibit repair (e.g., classic and/or alternative NHEJ) following nuclease-mediated cleavage of a cell's genome. In certain embodiments, the methods comprise the steps of: introducing one or more nucleases (and/or expression constructs or mRNAs that encode and express the nuclease(s)) into a host cell and introducing one or more inhibitors of proteins involved in repair of double- or single-stranded breaks (e.g., DNA-PKcs dependent error free classic or PARP-dependent alternative NHEJ) into the cell thereby increasing nuclease-mediated gene disruption in the cell. In certain embodiments, the inhibition of certain repair pathways results in the cell introducing more errors during repair, thereby increasing gene disruption following nuclease-mediate cleavage of the genome. See, also, FIG. 1.

In another aspect, described herein is a method for increasing targeted integration (e.g., via HDR) following nuclease-mediated cleavage in a cell. In certain embodiments, the methods comprise the steps of: (i) introducing one or more nucleases (and/or mRNAs or expression constructs that express the nuclease(s) and one or more single guide RNA if needed) along with one or more donor molecules into a host cell and (ii) introducing one or more inhibitors of proteins involved in the repair of double- or single-stranded breaks thereby increasing targeted integration of the one or more donor molecules (exogenous sequences) following nuclease cleavage in the cell. See, also, FIG. 1. In certain embodiments, the donor molecule comprises a sequence selected from the group consisting of a gene encoding a protein (e.g., a coding sequence encoding a protein that is lacking in the cell or in the individual or an alternate version of a gene encoding a protein), a regulatory sequence and/or a sequence that encodes a structural nucleic acid such as a microRNA or siRNA.

In any of the methods described herein, the inhibitor(s) may inhibit one or more of PARP1, Ku70/80, DNA-PKcs, XRCC4/XLF, Ligase IV, Ligase III, XRCC1, Artemis and/or Polynucleotide Kinase (PNK). In any of the methods described herein, the inhibitors may be small molecules, for example the PARP1 inhibitor Olaparib and/or the DNA-PKcs inhibitor NU7441. Furthermore, in any of the methods described herein, the nuclease may comprise, for example, a non-naturally occurring DNA-binding domain (e.g., an engineered zinc finger protein, an engineered TAL-effector DNA-binding protein, or an engineered DNA-binding domain from a homing endonuclease). In certain embodiments, the nuclease is a zinc finger nuclease (ZFN) or pair of ZFNs. In other embodiments, the nuclease is a TAL-effector domain nuclease (TALEN including at least fusions of TALE DNA-binding domains with any nuclease domain (e.g., endonuclease such as FokI, meganuclease to form mega-TAL or a TevI nuclease domain to form a cTALEN)) fusion protein or pair of TALENs. In certain embodiments, the nuclease is a CRISPR/Cas nuclease system comprising an engineered single guide RNA and a CRISPR/Cas nuclease.

In another aspect, the invention provides a host cell comprising one or more nucleases (and/or a polynucleotide encoding one or more nucleases) and/or the CRISPR/Cas nuclease system and an inhibitor of NHEJ repair pathways. In certain embodiments, the cell is a eukaryotic cell (e.g., a mammalian or plant cell). In some aspects, the host cell further comprises a donor DNA. In some aspects, the host cells are an established cell line while in other aspects, the host cell is a primary cell isolated from a mammal. In some aspects, the cell is a plant cell where the cell can be from a germplasm or a differentiated cell. In any of the methods described herein, the plant cell can comprise a monocotyledonous or dicotyledonous plant cell. In certain embodiments, the plant cell is a crop plant, for example maize. The nuclease(s) may be, for example, zinc finger nucleases (ZFNs), TAL-effector domain nucleases (TALENs), homing endonucleases and/or an engineered nuclease system comprising engineered single guide RNAs and the CRISPR/Cas nuclease. In some aspects, the donor DNA encodes a polypeptide, a regulatory region, or a structural nucleic acid.

In another aspect, the invention provides kits that are useful for increasing gene disruption and/or targeted integration following nuclease-mediated cleavage of a cell's genome. (e.g. ZFNs, TAL-effector domain nuclease fusion proteins, or engineered homing endonucleases or engineered guide RNAs with the CRISPR/Cas system). The kits typically include one or more nucleases that bind to a target site, one or more inhibitors of proteins involved in NHEJ and instructions for introducing the nucleases and inhibitors into the cells such that nuclease-mediated gene disruption and/or targeted integration is enhanced. Optionally, cells containing the target site(s) of the nuclease may also be included in the kits described herein. In certain embodiments, the kits comprise at least one construct with the target gene and a known nuclease capable of cleaving within the target gene. Such kits are useful for optimization of cleavage conditions in a variety of varying host cell types. Other kits contemplated by the invention may include a known nuclease capable of cleaving within a known target locus within a genome, and may additionally comprise a donor nucleic acid. In some aspects, the donor DNA may encode a polypeptide, a regulatory region or a structural nucleic acid. In some embodiments, the polypeptide is a reporter gene (e.g. GFP or GUS). Such kits are useful for optimization of conditions for donor integration or for the construction of specifically modified cells, cell lines, and transgenic plants and animals containing gene disruptions or targeted insertions.

These and other aspects will be readily apparent to the skilled artisan in light of disclosure as a whole.

BRIEF DESCRIPTION OF THE DRAWINGS

FIG. 2, panels A to E, shows increased error-prone (mutagenic) repair in Hepa 1-6 cells following treatment with albumin-specific ZFNs and DNA repair inhibitors. FIG. 2A is a schematic representation of experimental design. FIGS. 2B and 2C are gels depicting the percentage of mutagenic repair which was determined in duplicates by Surveyor™/Cell assay after day 3 (FIG. 2B) or day 10 (FIG. 2C). FIG. 2D shows the ZFN expression levels and the lack of apoptotic marker (PARP1 cleavage) by Western Blotting. The concentrations of the used inhibitors are shown as is the percent of mutagenic repair detected ("% indels"). FIG. 2E shows a genomic PCR (without Cell digestion) of both the mALB and the mCXCR4 loci. The percentages show the difference in band intensity between DMSO control and cells treated with NU7441+Olaparib.

FIG. 3, panels A through C, depict nuclease cleavage. FIG. 3A shows the distribution of genotypes (e.g. wild type, deletions or insertions) per condition. The left bar of each group depicts results of ZFN and DMSO-treated cells; the middle bar depicts results of cells treated with ZFNs and DNA-PKcsi and the right bar shows results of cells treated with ZFNs, DNA-PKcs inhibitor NU7441 either alone or in combination with PARP inhibitor Olaparib. FIG. 3B shows the total percentage of clones with mutagenic repair per condition.

FIG. 4, panels A to F, shows increased targeted integration in K562 or CHO K1 cells following treatment with DNA repair inhibitors. FIGS. 4E and E show targeted integration in CHO K1 cells where the donor was introduced either in a plasmid (FIG. 4E) or as a PCR fragment (FIG. 4F) into the glutamine synthetase (GS) locus.

FIG. 5, panels A and B, show targeted integration of a single-stranded donor after nuclease-mediated cleavage at the human CCR5 locus.

FIG. 6, panels A and B, show targeted integration of a single stranded donor in human cell lines. FIG. 6A depicts a gel showing integration of a donor in MCF10A, MCF7 or HEK293 cells into the AAVS1 locus in the presence of DNA-PKcs inhibitor NU7441. Lane designations for MCF10A lanes shown are as follows: Lane 1: ZFN+Oligo+DMSO; Lane 2: ZFN+Oligo+15 µM NU7441; Lane 3: ZFN+Oligo+20 µM NU7441; and Lane 4: Oligo+DMSO. Lane designations for MCF7 lanes shown are as follows: Lane 1: ZFN+Oligo+DMSO; Lane 2: ZFN+Oligo+10 µM NU7441; and Lane 3: Oligo+DMSO. Lane designations for HEK293 lanes shown are as follows: Lane 1: ZFN+Oligo+DMSO; Lane 2 ZFN+Oligo+10 µM NU7441; and Lane 3: Oligo+DMSO.

FIG. 7, panels A through C, depict targeted integration of ssOligo by single-stranded "nickase" ZFNs. See, e.g., U.S. Patent Publication No. 20100047805.

DETAILED DESCRIPTION

Described herein are compositions and methods for increasing the effectiveness of nuclease-mediated (e.g., ZFNs and/or TALENs such as FokI-TALE fusions, mega TALs, or compact TALENs) genomic modification by inhibiting cellular repair via classic DNA-PKcs dependent NHEJ ("error-free"), PARP1/2 dependent alternative NHEJ and PARP1/2 dependent SSB repair following cleavage of the cell's genome by a nuclease. Typically, inhibition of classic NHEJ and/or alternative (e.g., PARP1/2) repair pathways is achieved by inhibiting one or more enzymes involved in these NHEJ pathways, for example inhibiting DNA-dependent-protein kinase catalytic subunit (DNA-PKcs) and Poly-(ADP-ribose) polymerase 1/2 (PARP1) by small molecular inhibitors. See, e.g., O'Connor et al. (2007) *Oncogene* 26(56):7816-24.

Figure 1:
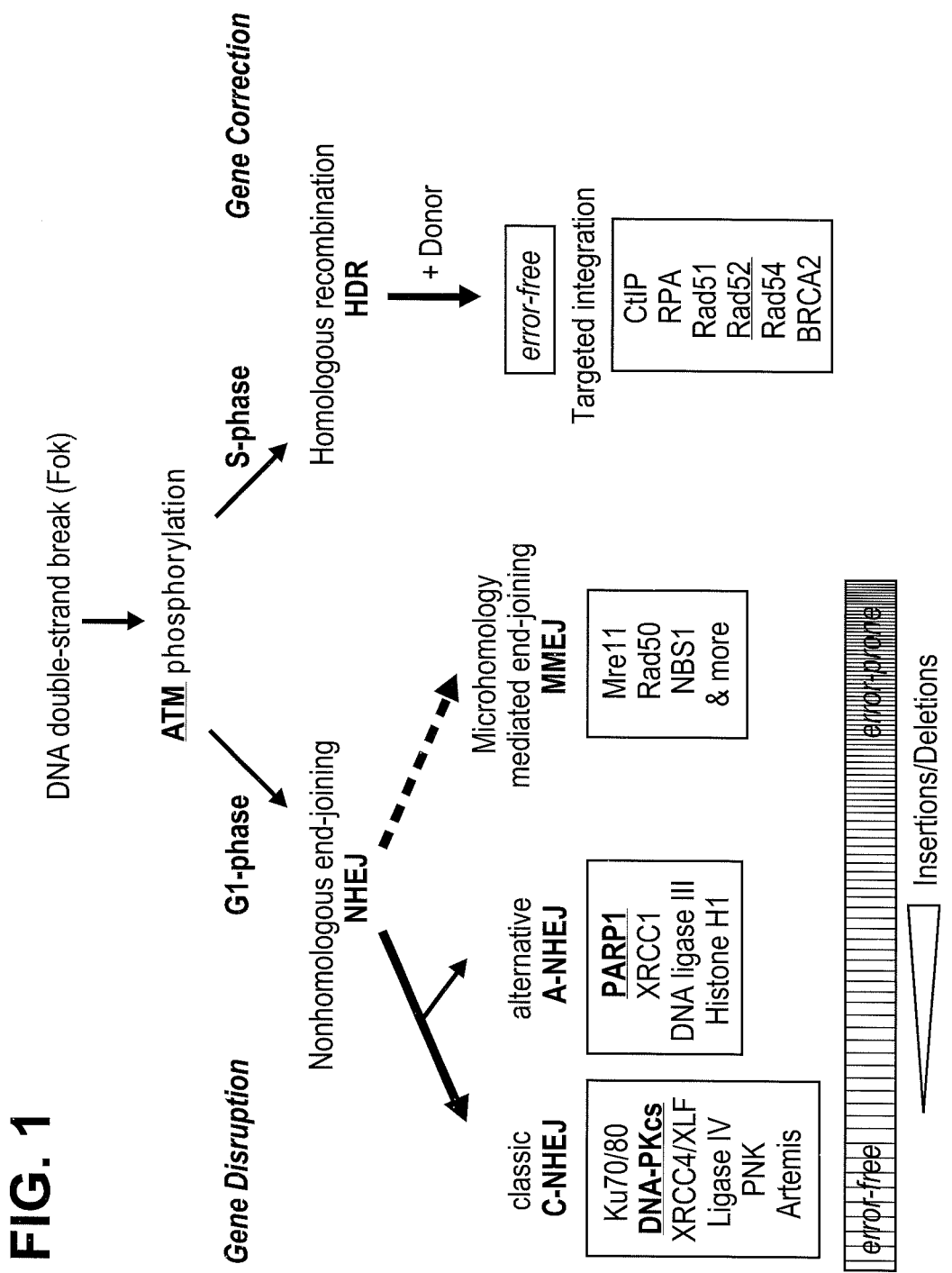
FIG. 1 is a schematic depicting hierarchy and manipulation of DNA repair pathways. A FokI-mediated DSB break can be repaired either by NHEJ or HDR. In G1-phase DNA repair by NHEJ is preferred and mostly occurs error-free by classic NHEJ via the DNA-PKcs complex. After failure or inhibition of this error-free pathway, more error-prone pathways like PARP1 mediated NHEJ or MMEJ are invoked by the cell, resulting in mutagenic repair and the generation of either point mutations, integrations and/or deletions ("indels"), which in turn can lead to gene disruption. As shown on the right portion of the Figure, if a DNA break persists and a DNA donor template is present, the HDR pathway can mediate integration of this DNA, for example to achieve gene correction. The respective protein targets of the used inhibitors or overexpression strategies are underlined.

The pathway of NHEJ in *S. cerevisiae* and mammals has been extensively characterized. In mammals, conserved proteins that are involved in classic NHEJ include the following: DNA-dependent protein kinase catalytic subunit (DNA-PKcs), the heterodimer Ku70/80, DNA ligase IV (Lig4), Xrcc4, Cernunnos/XLF and Artemis See, e.g., FIG. 1. Orthologs of these proteins have been identified also in yeast, fungi and plants with the exception of DNA-PKcs, which is not required for efficient NHEJ in these organisms. Because of its role in B-cell specific VDJ- and class switch recombination it has been suggested that DNA-PKcs has co-evolved with the adaptive immune system in vertebrates. DNA-PKcs and Ku70/80 are highly abundant nonhistone nuclear protein in human cells. However Ku70/80 is also found in the membrane and cytoplasm. Ku70/80 can shuttle from the cytoplasm to the nucleus in a manner that is dependent on the cell cycle status and external stimuli, like irradiation, alkylating agents, and hormones such as somatostatin. Ku70/80 has an extremely high affinity to DNA ends and thus rapidly binds to DSBs in living cells.

In response to DNA damage, the Mre11-Rad50-Xrs2 (MRX) complex in yeast and its counterpart in mammals, called Mre11-Rad50-Nbs1 (MRN), function early as a key player in the DNA damage sensing, signaling, and repair mechanism of both HR and NHEJ pathways. However, presumably in competition with the MRN complex, the DNA-PK complex consisting of DNA-PKcs and the Ku70/80 heterodimer also functions early in repair via Nonhomologous end-joining (NHEJ). NHEJ is initiated by the recognition and binding of the Ku heterodimer consisting of Ku70 and Ku80 to the exposed DNA ends. In mammals, the Ku70/80 heterodimer recruits DNA-PKcs and activates its kinase activity. Once the DNA-PKcs:Ku70/80 complex is bound to the damaged DNA ends, it can improve the binding equilibrium of the processing nuclease Artemis, the polymerases (µ and λ) and the ligase complex (XLF:XRCC4:Lig4). In this way, the DNA-PKcs: Ku70/80 complex serves as a scaffold of the subsequent protein assembly and stabilizes their enzymatic activities at a DNA end.

The next step involves the Lig4/XRCC4/XLF complex catalyzing the ligation and sealing the repair joint, thereby restoring the genomic integrity. It is important to note that sticky DNA ends without damaged bases (like the ones generated by FokI) can be easily rejoined without any further end-processing and subsequent insertions and/or deletions. Hence repair events following nuclease-mediated cleavage can be error-free. In other cases, Lig4 has an exclusive function in NHEJ by forming a complex with XRCC4 through the BRCT domain in the C-terminus of Lig4. This complex associates with Pol χ family polymerases, Pol μ, Pol λ, and terminal transferase, which fill in the short gaps generated during DNA end alignment and processing. The Lig4/XRCC4 complex also has an impact on the association of Cernunnos/XLF which promotes the ligation of mismatched and non-cohesive DNA ends. The NHEJ pathway that is DNA-PKcs:Ku70/80 dependent and is also called classic NHEJ (C-NHEJ).

Another NHEJ pathway has been identified in C-NHEJ deficient cells, which is Ku70/80 independent, called alternative NHEJ (A-NHEJ) (Jai et al (2012) *J Botany* doi: 10.1155/2012/989272). This pathway involves the activity of the single-strand break repair protein poly(ADP-ribose) polymerase 1 (PARP1), which can be substituted in the cell by the closely related PARP2. Therefore, inhibitors of this pathway tend to inhibit both members of the family, PARP1 and PARP2. PARP1/2 bind single-strand breaks with high affinity and can recruit their complex partners XRCC1 and DNA-ligase III, which mediate repair via DNA ligation. A crucial step in this pathway is the auto-modification of PARP1/2 via Poly(ADP)-ribosylation, which leads (as consequence of the negative charge of this modification) to the eventual release from DNA. If this auto-modification is blocked, PARP1/2 remain associated with the DNA and subsequent repair steps are impaired. Recent evidence has implicated PARP1/2 also in the repair of DSBs, in particular those which resemble two single strand breaks in close proximity to each other (like a FokI lesion) (see Wang et al, (2006) *Nucleic Acids Res.;* 34(21):6170-82).

If error-free (classic) and/or PARP1-dependent (alternative) repair pathways are inhibited, the cell will presumably then use error-prone DSB repair pathways (like for example MMEJ), which in turn increases gene disruption (e.g., deletions and/or additions) at the site cleaved by a nuclease. Accordingly, if gene disruption is the desired outcome of nuclease-mediated gene therapy, it is advantageous to increase the rate of error-prone DSB repair events to increase the amount of desired gene modification, also referred to as mutagenic repair (introduction of point mutations, insertions or deletions following repair of nuclease-mediated cleavage of the genome).

In addition, the present disclosure demonstrates that inhibition of error-free (classic) and/or PARP1-dependent (alternative) pathways as described herein increases targeted integration of a donor DNA molecule following induction of a double- or single-strand DNA break lesion using a nuclease. For gene correction it is essential that the lesion caused by the nuclease is not fully repaired before the integration of the corrective single- or double-stranded DNA donor template is achieved. Therefore, inhibiting of SSB and DSB repair pathways (e.g., via the use of commercially available inhibitors such as DNA-PKcs inhibitor NU7441) allow for efficient targeted integration.

In addition, inhibition of repair pathways as described herein dramatically increases the rate of ZFN-mediated targeted integration of a donor molecule after either induction of a double-stranded break (DSB) (e.g., using the wild typeFok1 nuclease) or a single-stranded break (SSB) (e.g., using the D450N Fok1 mutant "Nickase" as described in U.S. Patent Publication No. 20100047805).

Thus, the present disclosure maximizes the effects of a nuclease-mediated gene disruption and targeted integration strategy, in vivo, ex vivo and in vitro as small molecules known to inhibit repair in many species in a cell types can be readily administered in vivo, ex vivo and in vitro. Furthermore, increasing genomic modification by the nuclease(s) as described herein allows for the use of lower amounts of nuclease in the cell, thereby increasing the efficiency of genome editing in all cell types.

GENERAL

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acid.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526, incorporated by reference herein in its entirety.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 8,586,526; 6,140,081; 6,453,242; and 6,534,261; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 8,586,526; 5,789, 538; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 7,914,796; 8,034,598; 8,623,618 and U.S. Patent Publication No. 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value there between or there above), preferably between about 100 and 1,000 nucleotides in length (or any integer there between), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins, for example, a fusion between a DNA-binding domain (e.g., ZFP, TALE and/or meganuclease DNA-binding domains) and a nuclease (cleavage) domain (e.g., endonuclease, meganuclease, etc. and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Gene disruption" refers to additions and/or deletions and can occur via homology directed or non-homology directed repair mechanisms.

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soybean, canola (rapeseed), and alfalfa. Plant cells may be from any part of the plant and/or from any stage of plant development.

"Modulation" of gene expression refers to a change in the expression level of a gene. Modulation of expression can include, but is not limited to, gene activation and gene repression. Modulation may also be complete, i.e. wherein gene expression is totally inactivated or is activated to wild-type levels or beyond; or it may be partial, wherein gene expression is partially reduced, or partially activated to some fraction of wild type levels.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a DNA-binding domain (ZFP, TALE) is fused to a cleavage domain (e.g., endonuclease domain such as FokI, meganuclease domain, etc.), the DNA-binding domain and the cleavage domain are in operative linkage if, in the fusion polypeptide, the DNA-binding domain portion is able to bind its target site and/or its binding site, while the cleavage (nuclease) domain is able to cleave DNA in the vicinity of the target site. The nuclease domain may also exhibit DNA-binding capability (e.g., a nuclease fused to a ZFP or TALE domain that also can bind to DNA). Similarly, with respect to a fusion polypeptide in which a DNA-binding domain is fused to an activation or repression domain, the DNA-binding domain and the activation or repression domain are in operative linkage if, in the fusion polypeptide, the DNA-binding domain portion is able to bind its target site and/or its binding site, while the activation domain is able to upregulate gene expression or the repression domain is able to downregulate gene expression.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

Overview

Described herein are compositions and methods for increasing gene disruption (e.g., deletions, additions and/or targeted integration) following cleavage of a cell's genome by one or more nucleases. The compositions and methods described are effective in increasing gene disruption in a variety of cell types in which genomic modification is needed. In the methods described herein, DNA repair inhibitors are administered before, after or concurrently with the nucleases such that natural repair mechanisms are inhibited and gene disruption mediated by the nucleases enhanced. In addition, in the methods described herein multiple administrations (in any order) of the nucleases and/or inhibitors may be used. The rapid and efficient methods for increasing gene disruption by nucleases can be used to facilitate the generation of knock-out cell lines, to increase insertion of donor molecules into the target gene, in the creation of cells and/or transgenic organisms and to increase the therapeutic applications of nucleases in a variety of cell types.

Nucleases

The compositions and methods described herein increase nuclease-mediated gene modification. Thus, provided herein are nucleases, for example a fusion protein comprises a DNA-binding binding domain and cleavage (nuclease) domain. As such, gene modification can be achieved using a nuclease, for example an engineered nuclease. Engineered nuclease technology is based on the engineering of naturally occurring DNA-binding proteins.

A. DNA-Binding Domains

Any DNA-binding domain can be used in the nucleases used in the compositions and methods disclosed herein, including but not limited to a zinc finger DNA-binding domain, a TALE DNA binding domain, or a DNA-binding domain from a meganuclease.

In certain embodiments, the DNA-binding domain comprises a zinc finger protein. Preferably, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

In certain embodiments, the DNA binding domain is an engineered zinc finger protein that typically includes at least one zinc finger but can include a plurality of zinc fingers (e.g., 2, 3, 4, 5, 6 or more fingers). Usually, the ZFPs include at least three fingers. Certain of the ZFPs include four, five or six fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, wherein these regulatory domains can be transcriptional activation or repression domains.

In other embodiments, the DNA binding domain comprises a TALE DNA binding domain (see, U.S. Pat. No. 8,586,526, incorporated by reference in its entirety herein). The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et al (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas et al (1989) *Mol Gen Genet.* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Thus, in some embodiments, the DNA binding domain that binds to a target site in a target locus (e.g., globin or safe harbor) is an engineered domain from a TAL effector similar to those derived from the plant pathogens *Xanthomonas* (see Boch et al, (2009) *Science* 326: 1509-1512 and Moscou and Bogdanove, (2009) *Science* 326: 1501) and *Ralstonia* (see Heuer et al (2007) *Applied and Environmental Microbiology* 73(13): 4379-4384); U.S. Pat. Nos. 8,420,782 and 8,440,431 and U.S. Pat. No. 8,586,526.

An engineered zinc finger or TALE DNA binding domain can have a novel binding specificity, compared to a naturally-occurring zinc finger or TALE protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in WO 02/077227.

In addition, as disclosed in these and other references, zinc finger domains and/or multi-fingered zinc finger proteins or TALEs may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in WO 02/077227.

Selection of target sites; ZFPs or TALEs and methods for design and construction of fusion proteins (and polynucleotides encoding same) are known to those of skill in the art and described in detail in U.S. Pat. Nos. 6,140,081; 5,789, 538; 6,453,242; 6,534,261; 5,925,523; 6,007,988; 6,013, 453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-PpoI, I-SceII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. DNA-binding domains from meganucleases may also exhibit nuclease activity.

B. Cleavage Domains

Any nuclease may be used with any DNA-binding domain as described herein. The nuclease may comprise heterologous DNA-binding and cleavage domains (e.g., zinc finger nucleases; TALENs, and meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site). For example, engineering of homing endonucleases with tailored DNA-binding specificities has been described, see, Chames et al. (2005) *Nucleic Acids Res* 33(20):e178; Arnould et al. (2006) *J. Mol. Biol.* 355:443-458 and Grizot et al (2009) *Nucleic Acids Res* July 7 e publication. In addition, engineering of ZFPs has also been described. See, e.g., U.S. Pat. Nos. 6,534,261; 6,607,882; 6,824,978; 6,979,539; 6,933,113; 7,163,824; and 7,013,219.

In certain embodiments, the nuclease domain comprises a meganuclease (homing endonuclease) domain. Naturally-occurring meganucleases recognize 15-40 base-pair cleavage sites and are commonly grouped into four families: the LAGLIDADG family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-PpoI, I-SceII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. Thus, any meganuclease domain (or functional portion thereof) may be combined with any DNA-binding domain (e.g., ZFP, TALE) to form a nuclease. Furthermore, the nuclease domain may also bind to DNA.

DNA-binding domains from naturally-occurring meganucleases, primarily from the LAGLIDADG family, have been used to promote site-specific genome modification in plants, yeast, *Drosophila*, mammalian cells and mice, but this approach has been limited to the modification of either homologous genes that conserve the meganuclease recognition sequence (Monet et al. (1999), *Biochem. Biophysics. Res. Common.* 255: 88-93) or to pre-engineered genomes into which a recognition sequence has been introduced (Route et al. (1994), *Mol. Cell. Biol.* 14: 8096-106; Chilton et al. (2003), *Plant Physiology.* 133: 956-65; Puchta et al. (1996), *Proc. Natl. Acad. Sci. USA* 93: 5055-60; Rong et al. (2002), *Genes Dev.* 16: 1568-81; Gouble et al. (2006), *J. Gene Med.* 8(5):616-622). Accordingly, attempts have been made to engineer meganucleases to exhibit novel binding specificity at medically or biotechnologically relevant sites (Porteus et al. (2005), *Nat. Biotechnol.* 23: 967-73; Sussman et al. (2004), *J. Mol. Biol.* 342: 31-41; Epinat et al. (2003), *Nucleic Acids Res.* 31: 2952-62; Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication Nos. 20070117128; 20060206949; 20060153826; 20060078552; and 20040002092). In addition, naturally-occurring or engineered DNA-binding domains from meganucleases have also been operably linked with a cleavage domain from a heterologous nuclease (e.g., FokI) (also known as mega TALs).

In other embodiments, the nuclease is a zinc finger nuclease (ZFN). ZFNs comprise a zinc finger protein that has been engineered to bind to a target site in a gene of choice and cleavage domain or a cleavage half-domain.

As noted above, zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al., (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in WO 02/077227.

Selection of target sites; ZFNs and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, zinc finger domains and/or multi-fingered zinc finger proteins may be linked together using any suitable linker sequences, including for example, linkers of 5 or more amino acids in length. See, e.g., U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In any of the nucleases described herein, the nuclease can comprise an engineered TALE DNA-binding domain and a nuclease domain (e.g., endonuclease and/or meganuclease domain), also referred to as TALENs. Methods and compositions for engineering these TALEN proteins for robust, site specific interaction with the target sequence of the user's choosing have been published (see U.S. Pat. No. 8,586,526).

In some embodiments, the TALEN comprises a endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al., (2013) *Nucl Acid Res:* 1-13, doi: 10.1093/nar/gkt1224). In addition, the nuclease domain may also exhibit DNA-binding functionality.

In still further embodiments, the nuclease comprises a compact TALEN (cTALEN). These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et al (2013) *Nat Comm:* 1-8 DOI: 10.1038/ncomms2782). Any TALENs may be used in combination with additional TALENs (e.g., one or more TALENs (cTALENs or FokI-TALENs) with one or more mega-TALs).

Thus, nucleases as described herein also comprise a nuclease (cleavage domain, cleavage half-domain). As noted above, the cleavage domain may be heterologous to the DNA-binding domain, for example a zinc finger or TALE DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31, 978-982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer Bitinaite et al. (1998) Proc. Natl. Acad. Sci. USA 95:10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I or TALE-FokI fusions, two fusion proteins, each comprising a FokI cleavage half-domain, can be used to reconstitute a catalytically active cleavage domain. Alternatively, a single polypeptide molecule containing a zinc finger or TALE DNA binding domain and two Fok I cleavage half-domains can also be used. Parameters for targeted cleavage and targeted sequence alteration using zinc finger- or TALE-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Exemplary engineered cleavage half-domains of FokI that form obligate heterodimers include a pair in which a first cleavage half-domain includes mutations at amino acid residues at positions 490 and 538 of FokI and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (O) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Pat. Nos. 7,914,796 and 8,034,598 the disclosures of which are incorporated by reference in their entirety for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild-type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055). Engineered cleavage half-domains described herein can be prepared using any suitable method, for example, by site-directed mutagenesis of wild-type cleavage half-domains (Fok I) as described in U.S. Pat. Nos. 7,914,796; 8,034,598 and 8,623,618; and U.S. Patent Publication No. 20110201055.

Nuclease domains from any meganuclease or homing endonuclease can also be used in the nucleases described herein (e.g., operably linked to a DNA-binding domain). Non-limiting examples of homing endonucleases and meganucleases from which nuclease domains can be derived include I-SceI, I-CeuI, PI-PspI, PI-Sce, I-SceIV, I-CsmI, I-PanI, I-PpoI, I-SceIII, I-CreI, I-TevI, I-TevII and I-TevIII. Such nuclease domains may also bind to DNA.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Engineered cleavage half-domains described herein can be prepared using any suitable method, for example, by site-directed mutagenesis of wild-type cleavage half-domains (Fok I) as described for example, in U.S. Pat. Nos. 7,914,796; 8,034,598 and 8,623,618; and U.S. Patent Publication No. 20110201055.

Nuclease expression constructs can be readily designed using methods known in the art. See, e.g., United States Patent Publications 20030232410; 20050208489; 20050026157; 20050064474; 20060188987; 20060063231;

and International Publication WO 07/014,275. In certain embodiments, expression of the nuclease is under the control of an inducible promoter, for example the galactokinase promoter which is activated (de-repressed) in the presence of raffinose and/or galactose and repressed in presence of glucose. In particular, the galactokinase promoter is induced and the nuclease(s) expressed upon successive changes in the carbon source (e.g., from glucose to raffinose to galactose). Other non-limiting examples of inducible promoters include CUP1, MET15, PHO5, and tet-responsive promoters.

In certain embodiments, the nuclease comprises a CRISPR/Cas system. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Exemplary CRISPR/Cas nuclease systems targeted to safe harbor and other genes are disclosed for example, in U.S. Publication No. 20150056705.

Thus, the nuclease comprises a DNA-binding domain in that specifically binds to a target site in any gene into which it is desired to insert a donor (transgene).

Thus, the CRISPR/Cas system can be engineered to create a DSB at a desired target in a genome, and repair of the DSB can be influenced by the use of repair inhibitors to cause an increase in error prone repair.

C. Target Sites

As described in detail above, DNA domains in the nucleases (ZFNs, TALENs and/or RNAs of CRISPR/Cas) can be engineered to bind to any sequence of choice in a locus. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence. See, for example, U.S. Pat. Nos. 6,453,242 and 6,534,261, incorporated by reference herein in their entireties. Rational design of TAL-effector domains can also be performed. See, e.g., U.S. Pat. No. 8,586,526.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Pat. No. 8,586,526.

Additionally, single guide RNAs can be engineered to bind to a target of choice in a genome by commonly known methods known in the art for creating specific RNA sequences. These single guide RNAs are designed to guide the Cas9 to any chosen target site.

Inhibitors of DNA Repair

Any inhibitor of DNA repair pathways can be used in the practice of the present invention. Typically, the inhibitor is directed at an enzyme involved in error-free classic NHEJ and/or PARP1-mediated alternative NHEJ repair or their upstream regulation by post-translational modification via e.g. phosphorylation, ubiquitylation and sumoylation. The inhibitors may be small molecules and include, but are not limited to, small molecules, including commercially available small molecules that inhibit one or more proteins involved in DNA repair.

Non-limiting examples of PARP inhibitors (e.g., NU1025, Iniparib, Olaparib) include nicotinamides; isoquinolinones and dihydroisoquinolinones; benzimidazoles and indoles; phthalazin-1(2H)-ones and quinazolinones; isoindolinones and analogues and derivatives thereof; phenanthridines and phenanthridinones; benzopyrones and analogues and derivatives thereof; unsaturated hydroximic acid derivatives and analogues and derivatives thereof; pyridazines, including fused pyridazines and analogues and derivatives thereof; and/or other compounds such as caffeine, theophylline, and thymidine, and analogues and derivatives thereof. See, e.g., U.S. Pat. No. 8,071,579. DNA-PKcs inhibitors are known in the art include, but are not limited to, commercially available inhibitors such as NU7026, NU7441, etc. See, e.g., U.S. Pat. No. 6,974,867.

Additional, non-limiting examples of DNA repair pathways enzymes that can be inhibited for use in the present invention include: Ku70/80, XRCCR4/XLF, ligase IV (e.g. SCR7), PNK (e.g. A12B4C3), XRCC1, DNA ligase III and/or histone H1. Also, inhibitors targeting cell cycle checkpoint proteins like ATM (e.g. KU55933), CHK1/CHK2 (e.g. AZD7762 or CHIR-124) and ATR (e.g. VE 821) can be used to either synergistically to enhance the effects of specific DNA repair inhibitors or to prevent unintended side-effects like cell cycle arrest and/or apoptosis (see Ciccia et al. (2010) *Mol Cell* 40:179).

Any suitable amount of one or more DNA inhibitors may be used, so long as it is effective to increase nuclease activity. The particular concentrations used can be readily determined by one of skill in the art. In certain embodiments, between 0.5 µM to 25 µM concentrations is used, including any amount therebetween (e.g., 1 µM to 20 µM, 3 µM to 10 µM, etc.).

Donors

As noted above, insertion of an exogenous sequence (also called a "donor sequence" or "donor"), for example for correction of a mutant gene or for increased expression of a wild-type gene also can be carried out. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded and/or double-stranded and can be introduced into a cell in linear or circular form. See, e.g., U.S. Patent Publication Nos. 20100047805; 20110281361; and 20110207221. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A donor sequence may also be an oligonucleotide and be used for gene correction or targeted alteration of an endogenous sequence. The oligonucleotide may be introduced to the cell on a vector, may be electroporated into the cell, or may be introduced via other methods known in the art. The oligonucleotide can be used to 'correct' a mutated sequence in an endogenous gene (e.g., the sickle mutation in beta globin), or may be used to insert sequences with a desired purpose into an endogenous locus.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into an endogenous locus such that some (N-terminal and/or C-terminal to the transgene) or none of the endogenous sequences are expressed, for example as a fusion with the transgene. In other embodiments, the transgene (e.g., with or without additional coding sequences such as for the endogenous gene) is integrated into any endogenous locus, for example a safe-harbor locus, for example a CCR5 gene, a CXCR4 gene, a PPP1R12C (also known as AAVS1) gene, an albumin gene or a Rosa gene. See, e.g., U.S. Pat. Nos. 7,951,925 and 8,110,379; U.S. Publication Nos. 20080159996; 201000218264; 20100291048; 20120017290; 20110265198; 20130137104; 20130122591; 20130177983; and 20130177960 and 20150056705.

When endogenous sequences (endogenous or part of the transgene) are expressed with the transgene, the endogenous sequences may be full-length sequences (wild-type or mutant) or partial sequences. Preferably the endogenous sequences are functional. Non-limiting examples of the function of these full length or partial sequences include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Delivery

The proteins (e.g., ZFPs, TALENs, CRISPR/Cas) and/or polynucleotides encoding same, any donor polynucleotides and DNA repair inhibitors (e.g., small molecules) used in the described herein may be delivered to a target cell by any suitable means.

Small molecules (e.g., DNA repair inhibitors) can be readily delivered by any mechanism known in the art, including but not limited to, addition to cell culture media (to isolated cells) and/or injection (intravenous, intramuscular, etc.), topical applications, orally, etc. (to subjects). DNA repair inhibitors (e.g., small molecules) may be administered before, concurrently and/or after the nuclease(s) and/or optional donor are administered. One or more of the components may also be administered two or more times in any order, for example multiple administrations of nucleases and/or inhibitors serially and/or sequentially.

Methods of delivering proteins comprising nucleases as described herein are described, for example, in U.S. Pat. Nos. 6,453,242; 6,503,717; 6,534,261; 6,599,692; 6,607, 882; 6,689,558; 6,824,978; 6,933,113; 6,979,539; 7,013, 219; and 7,163,824, the disclosures of all of which are incorporated by reference herein in their entireties.

Zinc finger, TALE or CRISPR/Cas proteins as described herein may also be delivered using vectors containing sequences encoding one or more of the zinc finger proteins, zinc finger nucleases, TAL-effector domain proteins, TALENs and/or CRISPR/Cas protein(s). Donor encoding polynucleotides may be similarly delivered. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 8,586,526; 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more zinc finger protein-encoding sequences, one or more CRISPR/Cas-encoding sequences or one or more TALE-encoding sequences. Thus, when one or more nucleases or nuclease systems and/or donors are introduced into the cell, the nucleases or nuclease systems and/or donors may be carried on the same vector or on different vectors. When multiple vectors are used, each vector may comprise a sequence encoding one or multiple ZFPs, TALEs, nuclease comprising ZFPs and/or TALEs, CRISPR/Cas system and/or donors.

Conventional viral and non-viral based gene transfer methods can be used to introduce nucleic acids encoding engineered ZFPs, TALEs, nucleases comprising ZFPs and/or TALEs, CRISPR/Cas and/or donors in cells (e.g., mammalian cells) and target tissues. Such methods can also be used to administer nucleic acids encoding ZFPs, TALEs, nucleases comprising ZFPs and/or TALEs, CRISPR/Cas and/or donors to cells in vitro. In certain embodiments, nucleic acids encoding ZFPs, TALEs, nuclease encoding ZFPs and/or TALEs, CRISPR/Cas and/or donors are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, mRNA, artificial virions, and agent-enhanced uptake of DNA or can be delivered to plant cells by bacteria or viruses (e.g., *Agrobacterium, Rhizobium* sp. NGR234, *Sinorhizoboiummeliloti, Mesorhizobium loti*, tobacco mosaic virus, potato virus X, cauliflower mosaic virus and cassava vein mosaic virus. See, e.g., Chung et al. (2006) *Trends Plant Sci.* 11(1):1-4. Sonoporation using, e.g., the Sonitron 2000 system (RichMar) can also be used for delivery of nucleic acids. In a preferred embodiment, one or more nucleic acids are delivered as mRNA. Also preferred is the use of capped mRNAs to increase translational efficiency and/or mRNA stability. Especially preferred are ARCA (anti-reverse cap analog) caps or variants thereof. See U.S. Pat. Nos. 7,074,596 and 8,153,773, incorporated by reference herein in their entireties.

Additional exemplary nucleic acid delivery systems include those provided by Amaxa® Biosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. No. 5,049,386, U.S. Pat. No. 4,946,787; and U.S. Pat. No. 4,897,355) and lipofection reagents are sold commercially (e.g., Transfectam™, Lipofectin™ and Lipofectamine™ RNAiMAX). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485, 054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiamid et al (2009) *Nature Biotechnology* 27(7) p. 643).

The use of RNA or DNA viral based systems for the delivery of nucleic acids encoding engineered ZFPs, TALEs, ZFNs, TALENs and/or donors take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g. Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors is described in a number of publications, including U.S. Pat. No. 5,173,414; Tratschin et al., *Mol. Cell. Biol.* 5:3251-3260 (1985); Tratschin et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type virus. The vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6 and AAV8, AAV 8.2, AAV9, and AAV rh10 and pseudotyped AAV such as AAV2/8, AAV2/5 and AAV2/6 can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, AAV, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additionally, AAV can be produced at clinical scale using baculovirus systems (see U.S. Pat. No. 7,479,554.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NSO, SP2/0-Ag14, HeLa, HEK293 (e.g., HEK293-F, HEK293-H, HEK293-T), and perC6 cells, any plant cell (differentiated or undifferentiated) as well as insect cells such as *Spodoptera fugiperda* (Sf), or fungal cells such as *Saccharomyces, Pichia* and *Schizosaccharomyces*. In certain embodiments, the cell line is a CHO-K1, MDCK or HEK293 cell line. Additionally, primary cells may be isolated and used ex vivo for reintroduction into the subject to be treated following treatment with the nucleases (e.g. ZFNs or TALENs) or nuclease systems (e.g. CRISPR/Cas). Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells (CD34+), neuronal stem cells and mesenchymal stem cells.

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see, Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+(panB cells), GR-1 (granulocytes), and Iad (differentiated antigen presenting cells) (see Inaba et al., *J. Exp. Med.* 176:1693-1702 (1992)).

Stem cells that have been modified may also be used in some embodiments. For example, stem cells that have been made resistant to apoptosis may be used as therapeutic compositions where the stem cells also contain the ZFPs, TALEs, ZFNs, TALENs, CRISPR/Cas systems and/or donors of the invention. Resistance to apoptosis may come about, for example, by knocking out BAX and/or BAK using BAX- or BAK-specific nucleases (see, U.S. Patent Publication No. 2010/0003756) in the stem cells, or those that are disrupted in a caspase, again using caspase-6 specific ZFNs for example. Alternatively, resistance to apoptosis can also be achieved by the use of caspase inhibitors like Z-VAD-FMK (carbobenzoxy-valyl-alanyl-aspartyl-[O-methyl]-fluoromethylketone).

Vectors (e.g., retroviruses, adenoviruses, liposomes, etc.) containing therapeutic ZFPs, TALEs, ZFNs, TALENs, CRISPR/Cas system and/or donor nucleic acids can also be administered directly to an organism for transduction of cells in vivo. Alternatively, naked DNA or mRNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, U.S. Patent Publication No 20090117617.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

In contrast, when a transgene or fusion protein is administered in vivo for manipulation of a plant gene (see, "Nucleic Acid Delivery to Plant Cells" section below), either a constitutive, regulated (e.g., during development, by tissue or cell type, or by the environment) or an inducible promoter is used, depending on the particular use of the fusion protein. Non-limiting examples of plant promoters include promoter sequences derived from *A. thaliana* ubiquitin-3 (ubi-3) (Callis et al. (1990), *J. Biol. Chem.* 265-12486-12493); *A. tumifaciens* mannopine synthase (Amas) (Petolino et al., U.S. Pat. No. 6,730,824); and/or Cassava Vein Mosaic Virus (CsVMV) (Verdaguer et al., (1996), *Plant Molecular Biology* 31:1129-1139).

Nucleic Acid Delivery to Plant Cells

As noted above, DNA constructs may be introduced into (e.g., into the genome of) a desired plant host by a variety of conventional techniques. For reviews of such techniques see, for example, Weissbach & Weissbach *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9.

For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al. (1987) *Nature* 327:70-73). Alternatively, the DNA construct can be introduced into the plant cell via nanoparticle transformation (see, e.g., U.S. Patent Publication No. 20090104700, which is incorporated herein by reference in its entirety). Alternatively, the DNA constructs may be combined with suitable T-DNA border/flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al. (1984) *Science* 233:496-498, and Fraley et al. (1983) *Proc. Nat'l. Acad. Sci. USA* 80:4803.

In addition, gene transfer may be achieved using non-*Agrobacterium* bacteria or viruses such as *Rhizobium* sp. NGR234, *Sinorhizoboiummeliloti*, *Mesorhizobium loti*, potato virus X, cauliflower mosaic virus and cassava vein mosaic virus and/or tobacco mosaic virus, See, e.g., Chung et al. (2006) *Trends Plant Sci.* 11(1):1-4.

The virulence functions of the *Agrobacterium tumefaciens* host will direct the insertion of a T-strand containing the construct and adjacent marker into the plant cell DNA when the cell is infected by the bacteria using binary T DNA vector (Bevan (1984) *Nuc. Acid Res.* 12:8711-8721) or the co-cultivation procedure (Horsch et al. (1985) *Science* 227: 1229-1231). Generally, the *Agrobacterium* transformation system is used to engineer dicotyledonous plants (Bevan et al. (1982) *Ann. Rev. Genet.* 16:357-384; Rogers et al. (1986) *Methods Enzymol.* 118:627-641). The *Agrobacterium* transformation system may also be used to transform, as well as transfer, DNA to monocotyledonous plants and plant cells. See U.S. Pat. No. 5,591,616; Hernalsteen et al. (1984) *EMBO J* 3:3039-3041; Hooykass-Van Slogteren et al. (1984) *Nature* 311:763-764; Grimsley et al. (1987) *Nature* 325:1677-179; Boulton et al. (1989) *Plant Mol. Biol.* 12:31-40; and Gould et al. (1991) *Plant Physiol.* 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618).

Methods of introducing nuclease-encoding polynucleotides into plant cells are also described in U.S. Pat. Nos. 8,399,218 and 8,329,986 and U.S. Publication Nos. 20100257638; 20080182332; 20110167521; and 20110189775, incorporated by reference in their entireties herein.

The disclosed methods and compositions can be used to insert exogenous sequences into the multiple insertion site that has been inserted into the genome of a plant cell. This is useful inasmuch as expression of an introduced transgene into a plant genome depends critically on its integration site. Accordingly, genes encoding, e.g., herbicide tolerance, insect resistance, nutrients, antibiotics or therapeutic molecules can be inserted, by targeted recombination, into regions of a plant genome favorable to their expression.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and *Binding, Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al. (1987) *Ann. Rev. of Plant Phys.* 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna,* and *Zea.*

One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays (ELISA), where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the mRNA is present or the amount of mRNA has increased, it can be assumed that the corresponding transgene is being expressed. Other methods of measuring gene and/or encoded polypeptide activity can be used. Different types of enzymatic assays can be used, depending on the substrate used and the method of detecting the increase or decrease of a reaction product or by-product. In addition, the levels of polypeptide expressed can be measured immunochemically, i.e., ELISA, RIA, EIA and other antibody based assays well known to those of skill in the art, such as by electrophoretic detection assays (either with staining or western blotting). As one non-limiting example, the detection of the AAD-1 and PAT proteins using an ELISA assay is described in U.S. Patent Publication No. 20090093366, which reference is hereby incorporated by reference in its entirety herein. The transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

Fusion proteins (e.g., ZFNs) and expression vectors encoding fusion proteins can be administered directly to the plant for gene regulation, targeted cleavage, and/or recombination. In certain embodiments, the plant contains multiple paralogous target genes. Thus, one or more different fusion proteins or expression vectors encoding fusion proteins may be administered to a plant in order to target one or more of these paralogous genes (e.g. Zp15, see, U.S. Pat. No. 8,329,986) genes in the plant.

Administration of effective amounts is by any of the routes normally used for introducing fusion proteins into ultimate contact with the plant cell to be treated. The ZFPs are administered in any suitable manner, preferably with acceptable carriers. Suitable methods of administering such modulators are available and well known to those of skill in the art, and, although more than one route can be used to administer a particular composition, a particular route can often provide a more immediate and more effective reaction than another route.

Carriers may also be used and are determined in part by the particular composition being administered, as well as by the particular method used to administer the composition. Accordingly, there is a wide variety of suitable formulations of carriers that are available.

Applications

The disclosed compositions and methods can be used for any application in which it is desired to increase nuclease-mediated genomic modification in any cell type, including clinical applications nuclease-based therapies feasible in a clinical setting as well as agricultural (plant) applications. For example, the methods described herein will improve the therapeutic effect of ZFNs, TALENs, and/or CRISPR/Cas systems in the following scenarios: ex vivo and in vivo gene disruption (CCR5) in CD34+ cells (see, e.g., U.S. Pat. No. 7,951,925); ex vivo and in vivo gene correction of hemoglobinopathies in CD34+ cells (see, e.g., U.S. Publication Nos. 20140093913 and 20140080216); and/or ex vivo and in vivo gene addition to albumin locus for therapy of lysosomal storage diseases and hemophilias (see, e.g., U.S. Patent Publication Nos. 20140017212 and 20130177983).

In addition, the methods and compositions described herein can be used to generate model organisms and cell lines, including the generation of stable knock-out cells in any given organism. While ZFN, TALENs and CRISPR/Cas systems offer the ability to knock-out any given gene in cell lines or model organism, in the absence of selection marker these events however can be very rare. Accordingly, the methods described herein, which significantly increase the rate of targeted gene disruption, can be used to generate cell lines with new properties. This includes cell lines used for the production of biologicals like Hamster (CHO) cell lines or cell lines for the production of several AAV serotypes like human HEK 293 cells or insect cells like Sf9 or Sf21 or genomically-modified plants and plant lines.

The methods and compositions of the invention can also be used in the production of transgenic organisms. Transgenic animals can include those developed for disease models, as well as animals with desirable traits. Embryos may be treated using the methods and compositions of the invention to develop transgenic animals. In some embodiments, suitable embryos may include embryos from small mammals (e.g., rodents, rabbits, etc.), companion animals, livestock, and primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. In other embodiments, suitable embryos may include embryos from fish, reptiles, amphibians, or birds. Alternatively, suitable embryos may be insect embryos, for instance, a *Drosophila* embryo or a mosquito embryo.

Transgenic organisms contemplated by the methods and compositions of this invention also include transgenic plants and seeds. Examples of suitable transgenes for introduction include exogenous nucleic acid sequence that may comprise a sequence encoding one or more functional polypeptides (e.g., a cDNA), with or without one or more promoters and/or may produce one or more RNA sequences (e.g., via one or more shRNA expression cassettes), which impart desirable traits to the organism. Such traits in plants include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; drydown; standability; prolificacy; starch quantity and quality; oil quantity and quality; protein quality and quantity; amino acid composition; and the like. Of course, any two or more exogenous nucleic acids of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired. In certain embodiments, the exogenous nucleic acid sequence comprises a sequence encoding a herbicide resistance protein (e.g., the AAD (aryloxyalkanoatedioxygenase) gene) and/or functional fragments thereof.

The methods and compositions described herein can also be used to extend the dynamic range of nuclease activity for the purpose of in vitro testing, for the production of highly active ZFNs/TALENs and in in vitro assays (e.g., AAV/viral). In detail, the use of tissue-specific promoters in plasmid or AAV delivered ZFN constructs makes it very hard to test these in traditional cell lines where tissues-specific transcription markers may be expressed only at very low doses. The use of DNA repair inhibitors can overcome this limitation by increasing the ZFN activity to the point where it can be detected by Cell-Surveyor assay.

Kits

Also provided are kits for performing any of the above methods. The kits typically contain polynucleotides encoding one or more nucleases, one or more DNA repair inhibitors and/or donor polynucleotides as described herein as well as instructions for administering the DNA repair inhibitors into the cells into which the nucleases and/or donor polynucleotide are introduced. The kits can also contain cells, buffers for transformation of cells, culture media for cells, and/or buffers for performing assays. Typically, the kits also contain a label which includes any material such as instructions, packaging or advertising leaflet that is attached to or otherwise accompanies the other components of the kit.

The following Examples relate to exemplary embodiments of the present disclosure in which the nuclease comprises one or more ZFNs or one or more TALENs. It will be appreciated that this is for purposes of exemplification only and that other nucleases can be used, for instance homing endonucleases (meganucleases) with engineered DNA-binding domains and/or fusions of naturally occurring of engineered homing endonucleases (meganucleases) DNA-binding domains and heterologous cleavage domains, mega TALs, compact TALENs and nuclease systems such as CRISPR/Cas using engineered single guide RNAs.

EXAMPLES

Example 1: DNA Repair Inhibitors Increase Mutations in Nuclease-Treated Cells

As shown in FIG. 2A, Hepa 1-6 cells were transfected by Lipofectamine™ RNAiMAX with mRNA encoding an albumin-specific ZFN pair (see, U.S. Patent Application Nos. 20130177983 and 20130177968) and treated twice with small molecule inhibitors. In particular, the inhibitors Olaparib (PARP1-inhibitor) and NU7441 (DNA-PKcs inhibitor) were added 3 hours after mRNA delivery at concentration of 5 μM and 3-5 μM respectively. As a control, the ATM inhibitor KU55933 was added at a concentration of 10 μM (ATM has no direct role in DSB repair but is related to DNA-PKcs). After 15 hours, fresh inhibitors were added to the medium to counteract the decay of the inhibitors in the cell culture medium.

After a further 54 hours, cells were harvested and genomic DNA was prepared for Day 3 analysis by Surveyor™/Cell assay and DNA sequencing. For DNA sequencing the genomic target region of the ZFN was amplified by PCR, topo-cloned and 96 individual clones were sequenced. The sequences were analyzed and the results used to divide the clones into groups by the genome type (e.g. wild type genomes, those with insertions and/or deletions, and those with other modifications). At Day 3 harvest about a third of the cells were re-seeded in fresh medium without inhibitors and were grown until day 10 when they were harvested and analyzed by Surveyor™/Cell assay.

Figure 3A:
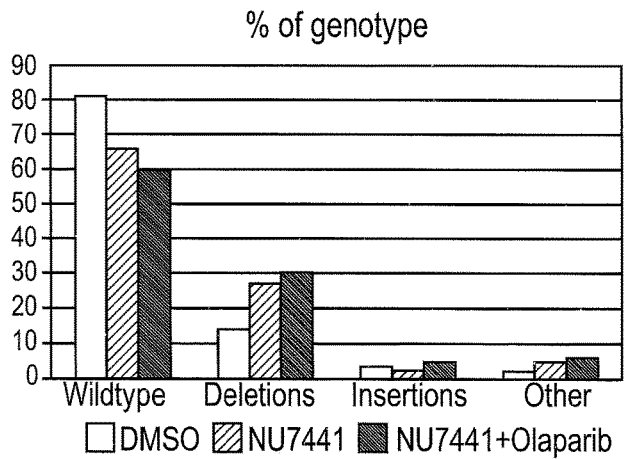
FIGS. 3A and 3B are graphs showing the percentage of mutagenic repair as determined by sequencing of subcloned genomic DNA after PCR of the target locus albumin at day 3 following treatment of Hepa 1-6 cells with ZFNs and DNA repair inhibitors.
Figure 3B:
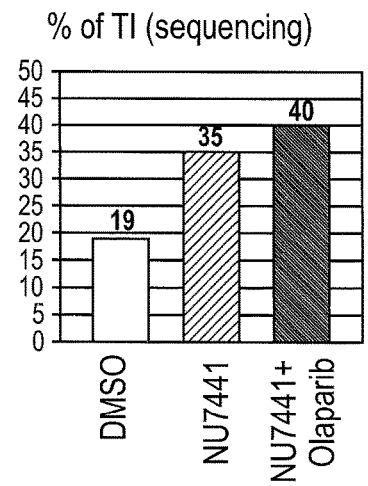
Figure 3C:
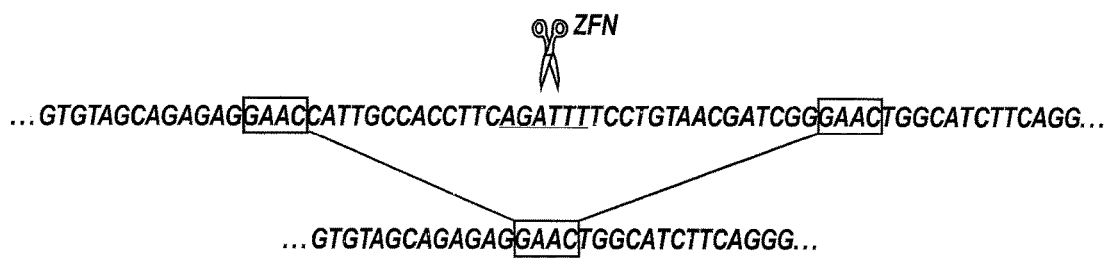
FIG. 3C (SEQ ID NO:1, top panel) illustrates the nuclease cut (indicated by scissors) and the two regions of microhomology near the cleavage site are indicated by boxes. The bottom panel (SEQ ID NO:2) shows deep sequencing analysis of the percentage of repaired DSBs at a specific site where the use of repair inhibitors increased the frequency of microhomology mediated end joining (MMEJ) from about 0.3% in cells without inhibitors up to between 2.1 and 2.6% when repair inhibitors are used.

As shown in FIG. 2 and FIG. 3C, the addition of the ATM inhibitor KU55933 caused a slight decrease of mutagenic repair. In contrast, a 2-3-fold increase of mutagenic repair ("% indels") was observed after the addition of DNA-PKcs-inhibitor alone (NU7441) or in combination with PARP1/2-inhibitor (Olalparib). This effect was somewhat reduced at Day 10, where the increase of mutagenic repair was still about 2-fold. The results indicate that most cells recover after withdrawal of the small molecule inhibitors and resume a normal cell cycle. The expression levels of ZFNs after 28 hours were significantly lower after inclusion of any inhibitor (FIG. 2D), ruling out the possibility that higher ZFN expression due to cell cycle arrest is causing the higher Indel percentage after NU7441+Olaparib treatment.

To exclude the possibility that cell death contributes to the somewhat weaker parental PCR band in FIGS. 2B and 2C, radioactive genomic PCR was carried out at both the mALB and the mCXCR4 locus, respectively (FIG. 2E). Then the band intensity was compared between DMSO control and the cells treated with NU7441 and Olaparib. If cell death was causing the decrease in band intensity in the NU7441+Olaparib samples, both loci should be equally affected (by DNA fragmentation) and show weaker PCR amplification. However, while at the mALB (ZFN target locus) the band intensity was reduced by 36%, the mCXCR4 was marginally higher (3%). This indicates that cell death is not responsible for the observed differences in band intensity.

The sequencing data shown in FIG. 3 (from Day3) confirmed the 2-fold increase of mutagenic repair after DNA-PKcs inhibition alone. Further, most of these events were small deletions (FIG. 3A).

FIG. 3C shows the percent of MMEJ (microhomology-mediated end joining) utilized by cells following cleavage.

As illustrated, the nuclease cut (indicated by scissors) the genome. The two regions of microhomology near the cleavage site are indicated by boxes. If repair occurs via MMEJ, the cleaved DNA will be resected to these areas of microhomology and then joined. This junction was then detected by deep sequence analysis. As shown in FIG. 3C, the percent of MMEJ detected by deep sequencing at day 3 or day 10 showed an increase in MMEJ usage observed in the presence of classic NHEJ and alternative NHEJ inhibitors was nearly ten-fold, supporting that there is a hierarchy of DNA repair pathways.

In summary, the DSB repair pathways can be manipulated by the use of specific small molecule inhibitors in order to increase mutagenic repair events.

Example 2: Increase of Nuclease-Mediated Targeted Integration of a ssOligo in K562 and CHO K1 Cells Using DNA-PKcs Inhibitor A. ZFNs K562 cells were transfected by Amaxa® electroporation system with plasmid DNA encoding a CCR5-specific ZFN pair (see, U.S. Pat. No. 7,951,925) and a single-stranded oligonucleotide (ssOligo) (120 bp) which has homology to the target region and harbors a unique restriction site (Avr II). The cells then were treated twice with small molecule inhibitors described in Example 1 (outlined in FIG. 2A). In particular, the inhibitors Olaparib (PARP1/2-inhibitor) and NU7441 (DNA-PKcs-inhibitor) were added 5 hours after the ZFN-encoding DNA delivery at concentration of 5 μM and 3 μM, respectively. As a control, the ATM inhibitor KU55933 was added at a concentration of 10 μM. After 15 hours, fresh inhibitors were added to the medium to counteract the decay of the inhibitors in the cell culture medium. After a further 54 hours, the cells were harvested and genomic DNA was prepared for Day 3 analysis by Surveyor™/Cell assay, RFLP analysis and DNA sequencing.

The RFLP assay was carried out by digestion of the PCR amplified target locus with a restriction enzyme cutting in the integrated ssOligo. For DNA sequencing, the genomic target region of the ZFN was amplified by PCR, topo-cloned and 96 individual clones were sequenced.

As shown in FIG. 4 (Panels A to C), the addition of the ATM inhibitor KU55933 had no effect on targeted integration. In contrast, a 2-3-fold increase of targeted integration was observed after the addition of DNA-PKcs inhibitor. This increase was observed both by the RFLP assay and by 96 colony sequencing. The addition of PARP 1/2 inhibitor did not further increase the efficiency of target integration. The expression levels of ZFNs were slightly higher after inclusion of any inhibitor, which could positively influence both cutting and targeted integration. This is most likely due to a cell cycle arrest in the treated cells, which is supported by the about 50% lower cell count at Day3 (FIG. 4C). However, only addition of the DNA-PKcs inhibitor NU7441 (by itself or with Olaparib) led to higher targeted integration rates, so the contribution of higher ZFN expression is negligible.

Figure 4A:
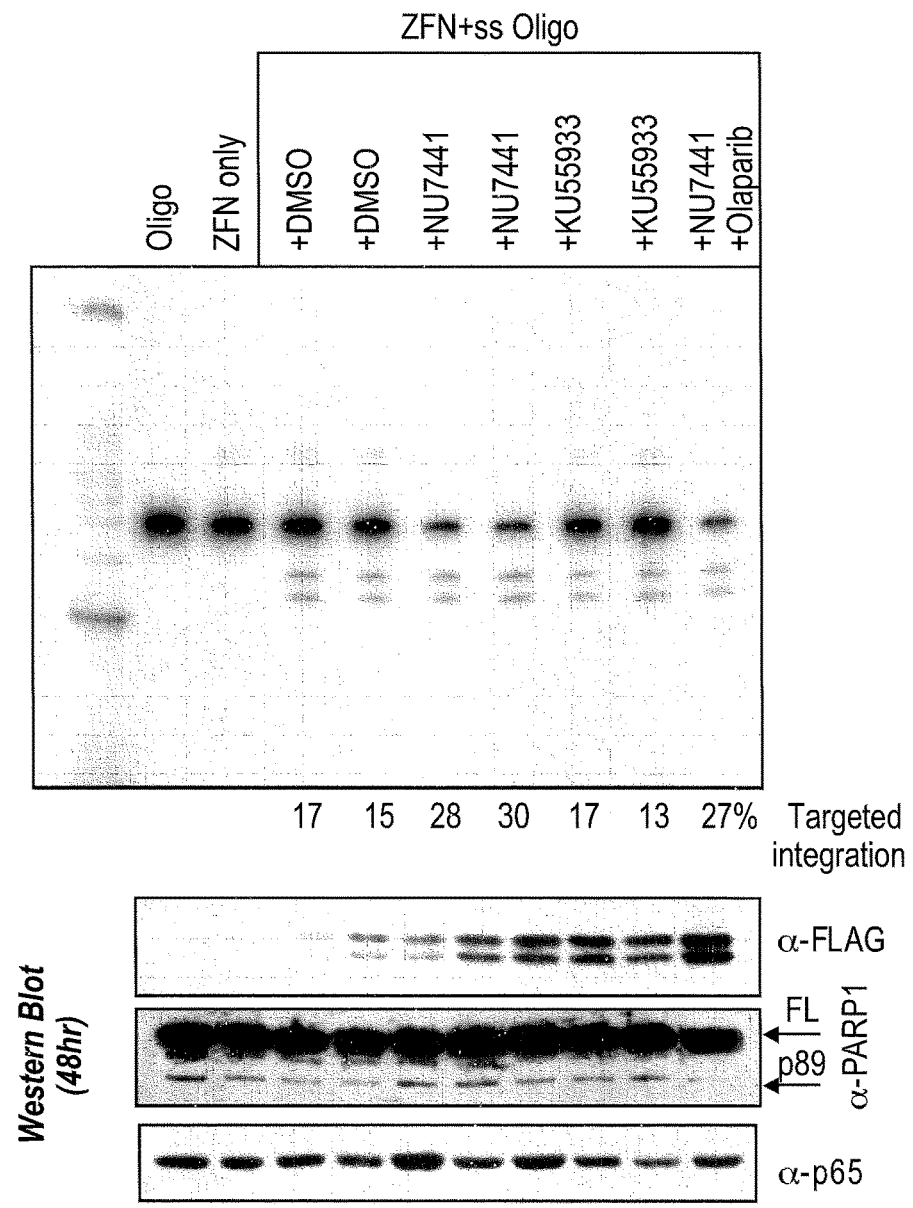
FIG. 4A shows the percentage of targeted integration of a single stranded Oligo (ssOligo) in K562 cells, which was determined in duplicates by RFLP assay. The lower portion of the panel shows the ZFN expression levels and the lack of apoptotic marker (PARP1 cleavage) by Western Blotting after 48 hrs.
Figure 4B:
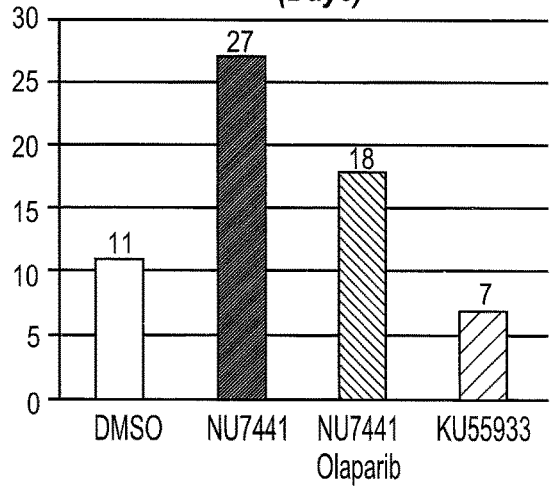
FIG. 4B is a graph showing the percentage of targeted integration (as determined by sequencing of subcloned genomic DNA after PCR) of the target locus CCR5.
Figure 4C:
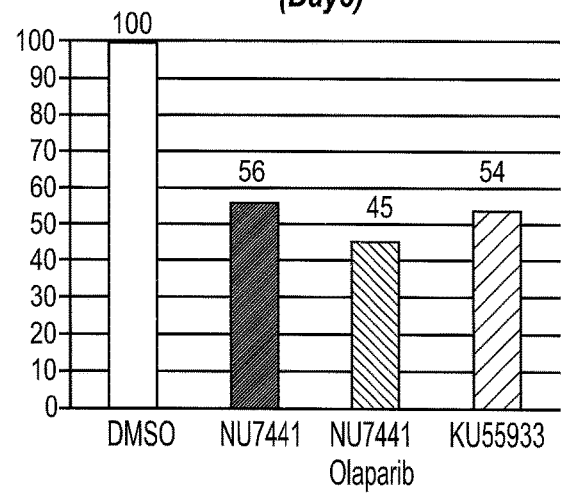
FIG. 4C is a graph showing the relative percentage of cell counts from the same samples.
Figure 4D:
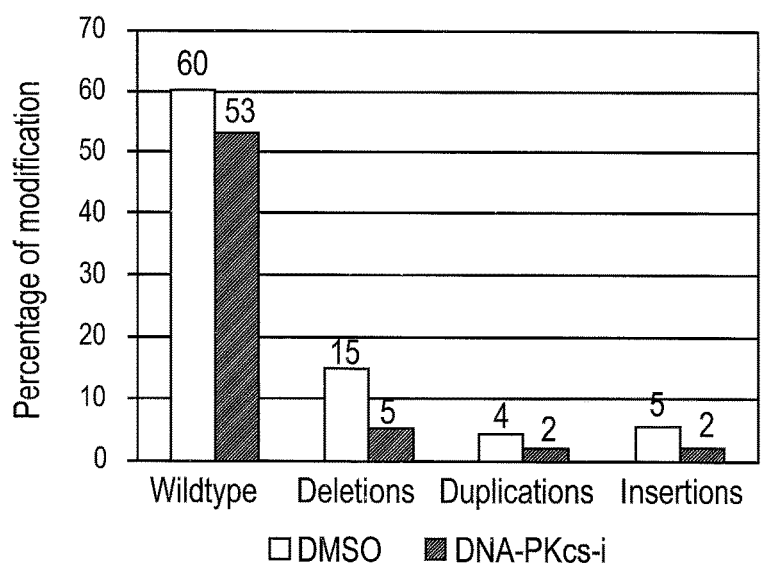
FIG. 4D is a graph showing the percentage of alternative repair events which was also determined by sequencing.

Interestingly, sequencing revealed that the increase in targeted integration does not only come at the expense of wild type alleles, but also deletions, duplications and insertions (compare FIG. 4B with 4D). This suggests that the use of repair inhibitors can make targeted integration more specific and can avoid unintended DNA repair events.

Analysis at Day 10 demonstrated that the increase of targeted integration after DNA-PKcs inhibition was virtually unchanged from Day3. This indicates that most cells recover after withdrawal of the small molecule inhibitors and resume a normal cell cycle.

The use of DNA PKcs inhibitors during insertion of a double stranded donor in CHO K1 cells was also tested. For this experiment, a donor that was delivered either via a plasmid (FIG. 4E) or via a PCR fragment (FIG. 4F). Briefly, CHO K1 cells were transfected with Nucleofector Kit V on an Amaxa® instrument. The transfection components and their dosages were as follows: one million CHO K1 cells suspended in 100 μl of Nucleofection™ Solution V; 4 μg each of two in vitro transcribed ZFN mRNAs engineered for inducing DSBs at the glutamine synthetase locus (GS) in CHO cells (see, e.g., U.S. Pat. No. 8,153,399); 2 μg (FIG. 4E) or 4 μg (FIG. 4F) of in vitro transcribed CHO or human Rad52 mRNA; 10 μg of plasmid donor (3.8 kb) or PCR fragment donor (1.1 kb). The plasmid donor and the PCR fragment donor both carried the same target integration sequence, containing two 500 bp homologous arms, two loxP sites, and a multiple cloning site.

DNA-PKcs inhibitor NU7026 or NU7441 was added into 2 ml per well of pre-warmed culture medium in a 6-well plate at concentration of 20 μM or 16 respectively, before transfected cells were added into the medium. Cells were grown in the inhibitor-containing medium for 24 hours at 37° C. and 5% $CO_2$. The medium was then replaced with fresh medium without inhibitor. DMSO was used as inhibitor blank control. For genomic DNA preparation, cells were harvested 3 days after transfection. Genomic DNA was amplified by PCR with a pair of primers located on the upstream and downstream of the integration sequence. RFLP analysis was carried out by digesting purified PCR product with Hind III and resolving the digestion reaction on 1% agarose gel.

As shown in FIG. 4E, the application of DNA-PKcs inhibitor NU7026 in conjunction with the addition of Rad52 mRNA led to a 2- to 4-fold increase in the plasmid donor-based target integration, notwithstanding that NU7026 alone exhibited no apparent increase under the condition. The results show that the DNA-PKcs inhibitor and Rad52 mRNA had a synergistic effect on promoting plasmid-based target integration. Furthermore, as shown in FIG. 4F, the addition of DNA-PKcs inhibitor NU7441 increased the PCR fragment donor-based target integration by about 5-fold, regardless of whether or not the PCR fragment donor carried cloning vector sequences at the ends. The observed differences between the DNA-PKcs inhibitors NU7026 and NU7441 may be attributed to the fact that NU7441 is more specific and more potent than NU7026.

B. TALENs

In order to demonstrate that TALEN-mediated targeted integration could also be enhanced by the use of DNA repair inhibitors, we performed a similar experiment with the TALEN pair 101028:101036, which also targets the human CCR5 locus. See, e.g., U.S. Pat. No. 8,586,526. K562 cells were transfected by AMAXA with plasmid DNA encoding either hCCR5 TALENs or ZFNs and then the cells were treated with DMSO or DNA-PKcs inhibitor NU7441. Cells were harvested at Day 3 and Day 10 and genomic PCR was analyzed after PCR by deep sequencing.

Figure 5A:
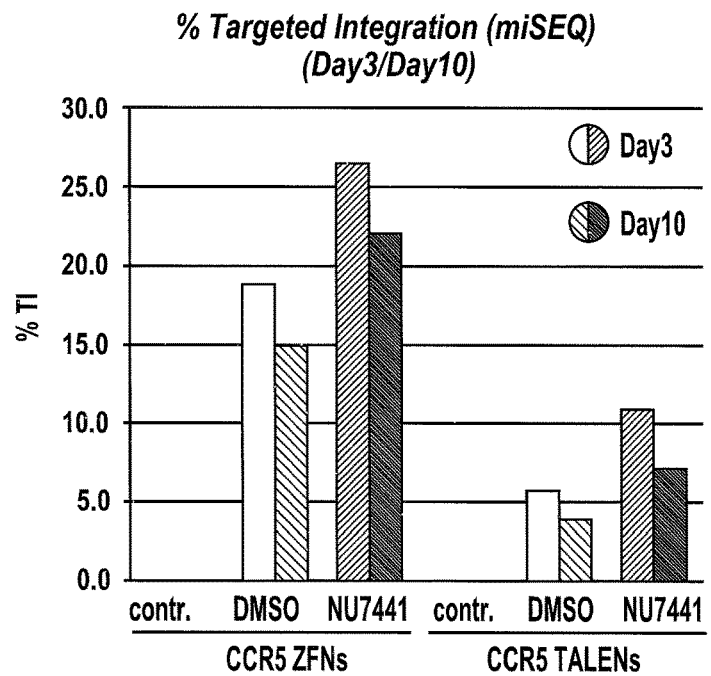
FIG. 5A depicts the total percentage of targeted integration at Day3 and Day10 in cells treated with hCCR5-specific ZFNs or TALENs and DMSO or DNA-PKcs inhibitor NU7441.
Figure 5B:
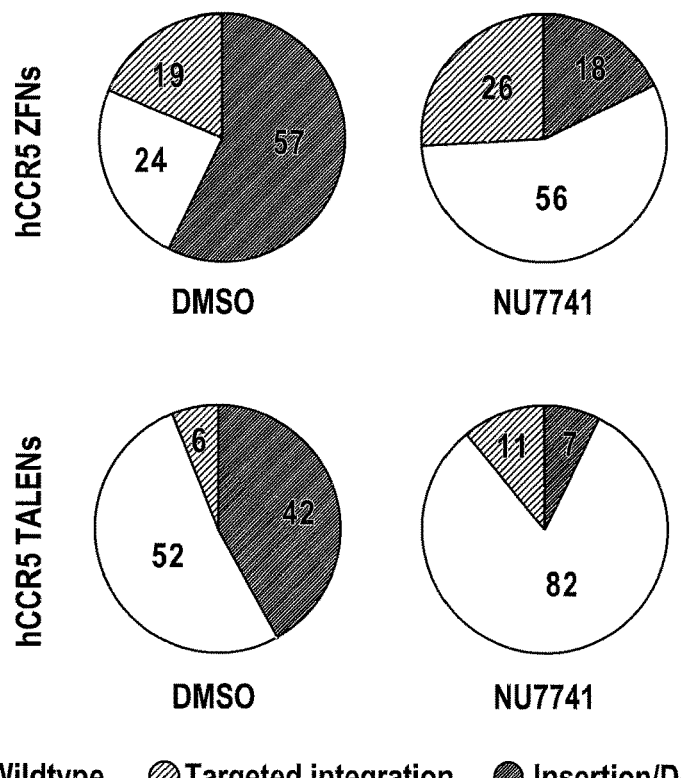
FIG. 5B are pie graphs showing the relative percentage of wild type, targeted integration and other Indel events, respectively, of cells treated under the indicated conditions. The data of FIGS. 5A and 5B was generated by deep sequencing.

As shown in (FIG. 5, as with ZFN-mediated cleavage, TALEN-mediated targeted integration up to two fold (FIG. 5A) at Day 3. In line with the ZFN data described above, we also observed with TALENs that after NU7441 treatment more than half of all genome editing events are now targeted integrations and that unwanted mutagenic events (Indels) were drastically reduced (FIG. 5B). The difference in behavior at day 10 where ZFN-mediated TI events further increased and TALEN-mediated events decrease could be attributed to the higher specificity of the CCR5 ZFNs used (e.g., highly optimized ZFNs) as opposed to the first generation CCR5 TALENs, which have yet to undergo further optimization.

Thus, the data demonstrates that both ZFN- and TALEN-mediated cleavage can be manipulated with the same inhibitors.

These results show that DSB repair pathways can be manipulated by the use of specific small molecule inhibitors in order to increase the efficiency and the specificity of targeted integration.

Example 3: Increase of Targeted Integration of a ssOligo in HEK293 or CD34+ Cells Using DNA-PKcs Inhibitors We next used the inhibitors to measure their effect on targeted integration of single-stranded donors. Briefly, HEK293 and MCF7 cells were transfected with Nucleofector Kit V and MCF10A cells were transfected with Nuleofector™ Kit L on an Amaxa® instrument. The transfection components and their dosages were as follows: 0.8 million cells suspended in 100 µL of nucleofection solution; 3 µg each of two in vitro transcribed ZFN mRNAs engineered for inducing DSBs at the AAVS1 locus in human cells (see, e.g., U.S. Pat. No. 8,110,379); 0.3 nmol of a 100-nt ssDNAoligo donor. The oligo donor carried a HindIII restriction site at the position of 20 bp upstream of the ZFN cleavage site, and the HindIII site was used as marker for target integration analysis by RFLP.

DNA-PKcs inhibitor NU7441 was added into 2 ml per well of pre-warmed culture medium in a 6-well plate at concentration of 10 µM for HEK293 and MCF7, and 15 or 20 µM for MCF10A before transfected cells were added into the medium. Cells were grown in the inhibitor-containing medium for 24 hours at 37° C. and 5% $CO_2$. The medium was then replaced with fresh medium without inhibitor. DMSO was used as inhibitor blank control. For genomic DNA preparation, HEK293 and MCF10A cells were harvested 3 days after transfection, and MCF7 cells were harvested 5 days after nucleofection. Genomic DNA was amplified by PCR with a pair of primers located on the upstream and downstream of the ssDNAoligo donor sequence. RFLP analysis was carried out by digesting purified PCR product with Hind III and resolving the digestion reaction on 10% acrylamide gel.

As shown in FIG. 6, the results demonstrated that the use of NU7441 increased the targeted integration of a single stranded donor in HEK293 cells (see, e.g., FIG. 6A).

The previous experiments demonstrated that small molecule inhibitors could be used to increase the efficiency and the specificity of targeted integration of double stranded and single stranded donor sequences in cell lines. To demonstrate that small molecule inhibitors could also be used to increase the efficiency and the specificity of targeted integration in primary cells, a small molecule inhibitor (NU7441) was added to CD34+ progenitor cells.

Specifically, donor derived CD34+ cells were transfected 3 days after culture in medium suppressing differentiation. This was carried out by the BTX electroporation system with mRNA DNA encoding a CCR5-specific ZFN pair and a ssOligonucleotide (120 bp) which has homology to the target region and harbors a unique restriction site (Avr II). The cells were then treated twice with small molecule inhibitors as described in Example 1. In particular, the inhibitor NU7441 (DNA-PKcs-inhibitor) was added 3 hours after mRNA delivery at a concentration of 3 µM. After 15 hours, fresh inhibitors were added to the medium to counteract the decay of the inhibitors in the cell culture medium. After a further 54 hours, cells were harvested and genomic DNA was prepared for Day 3 analysis by DNA sequencing. For DNA sequencing the genomic target region of the ZFN was amplified by PCR, topo-cloned, and 96 individual clones were sequenced.

Figure 6B:
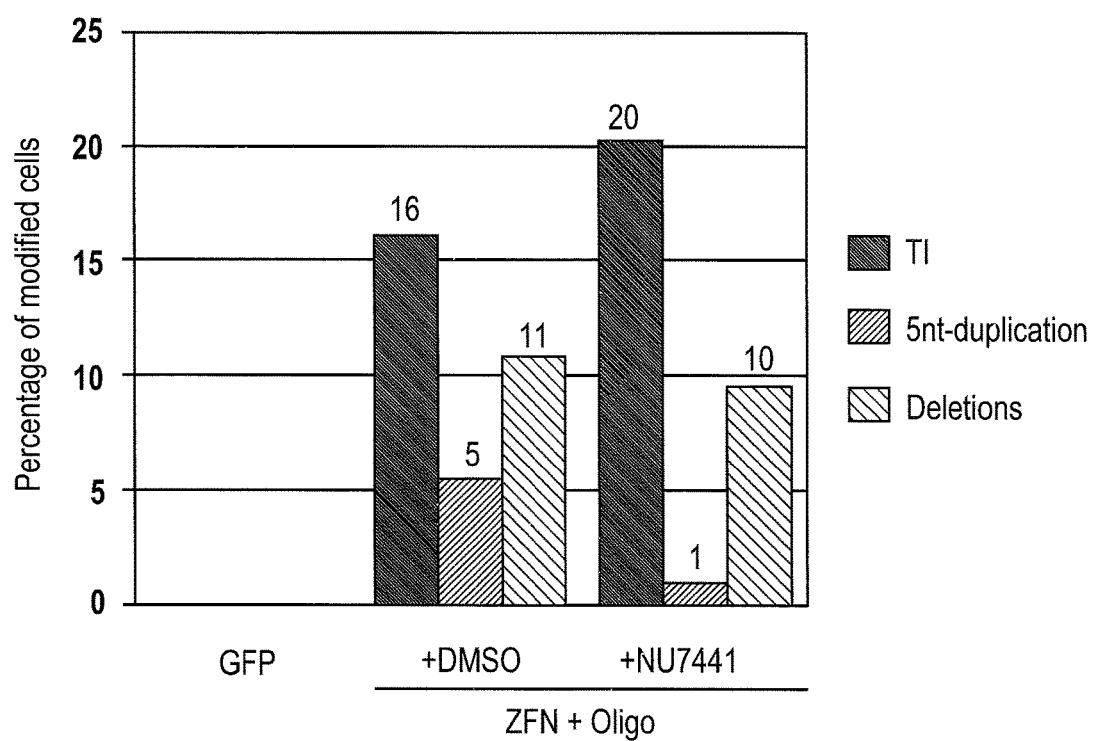
FIG. 6B is a graph showing increased targeted integration in CD34+ cells after DNA-PKcs inhibition via NU7441. The percentages of targeted integration, and 5-nucleotide duplications and deletions were determined by sequencing of subcloned genomic DNA after PCR of the target locus CCR5.

As shown in FIG. 6B, the addition of DNA-PKcs inhibitor results in a slight increase of targeted integration in CD34+ cells at the expense of 5-nucleotide duplications and deletions.

Thus, DSB repair pathways can be manipulated by the use of specific small molecule inhibitors in order to increase the efficiency and the specificity of targeted integration in primary cells.

Example 4: Increase of Targeted Integration of a ssOligo in K562 Cells by Nickase and DNA-PKcs/Parp Inhibitor Treatment K562 cells were transfected by Amaxa electroporation system with plasmid DNA encoding a CCR5-specific ZFN pair (see, U.S. Pat. No. 7,951,925) and a single-stranded oligonucleotide (ssOligo) (120 bp) which has homology to the target region and harbors a unique restriction site (Avr II). In contrast to previous experiments, the ZFN pair included of a wild type FokI ZFN (8196-WT) and a mutant Fok1 ZFN (8267-D450N) (see, U.S. Pat. Nos. 7,914,796; 8,034,598 and 8,623,618), the ZFN pair used in this experiment cleaves on one strand of DNA at the target site and hence serves as a "nickase." See, U.S. Patent Publication No. 20100047805. Due to the less deleterious nature of this kind of DNA damage, recombination events mediated by ssDNA breaks may be preferable over DSBs. However, the frequency of gene modification mediated via ssDNA breaks is very low. DNA-PKcs and PARP inhibitors were used in an attempt to increase the frequency of gene modification mediated via ssDNA breaks ("nicks").

Briefly, the transfected K562 cells were treated twice with either PARP1/2 inhibitor (Olaparib-5 µM) or DNA-PKcs inhibitor (NU7441-3 µM) 5 hours and 15 hours after transfection to counteract the decay of the inhibitors in the cell culture medium. After a further 54 hours, cells were harvested and genomic DNA was prepared for Day 3 analysis by Surveyor™/Cell assay, RFLP analysis and DNA sequencing as described in Example 1. The RFLP assay was carried out by digestion of the PCR amplified target locus with a restriction enzyme cutting in the integrated ssOligo. For DNA sequencing, the genomic target region of the ZFN was amplified by PCR, topo-cloned, and 96 individual clones were sequenced.

Figure 7A:
FIG. 7A is a schematic representation of experimental design.
Figure 7B:
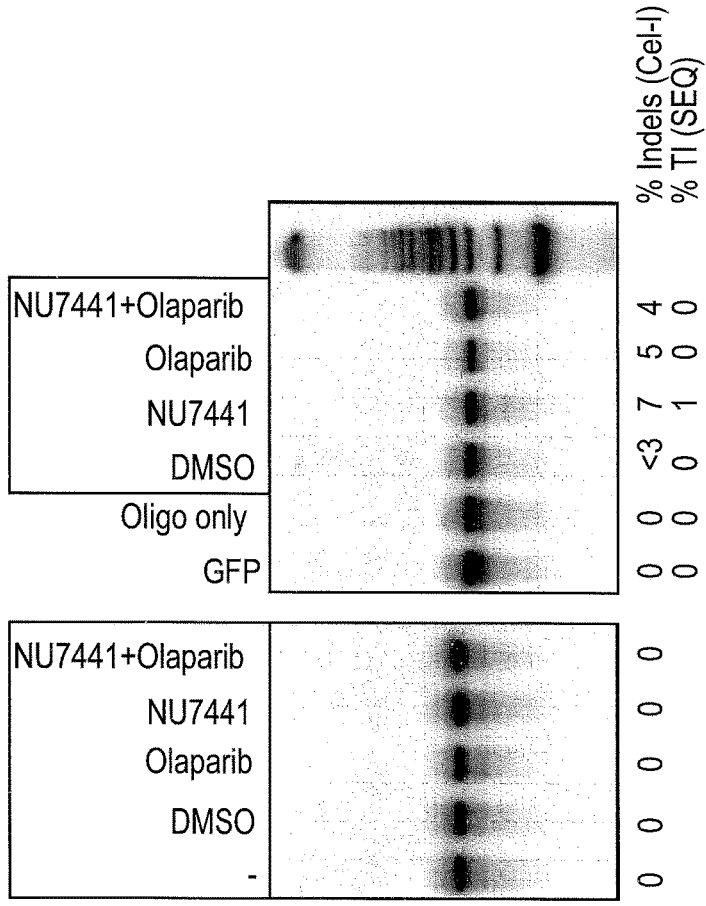
FIG. 7B shows Surveyor™/Cell data and sequencing data for K562 cells treated with Nickase, ssOligo and DNA repair inhibitors.

As shown in FIGS. 7A and B, nickase-only treatment did not yield any detectable levels of Cell signal, (no indels) even in the presence of DNA repair inhibitors. However, when a single-stranded oligonucleotide was co-transfected with the Nickase ZFNs a very low Cell signal was detected in the untreated cells and a robust signal (7% and 5% indels) was detected after DNA-PKcs and PARP1/2 inhibition. When we sequenced these samples, only one of 96 clones treated with DNA-PKcs inhibitor yielded a non-WT sequence, which represented a perfect targeted integration of the ssOligo.

Figure 7C:
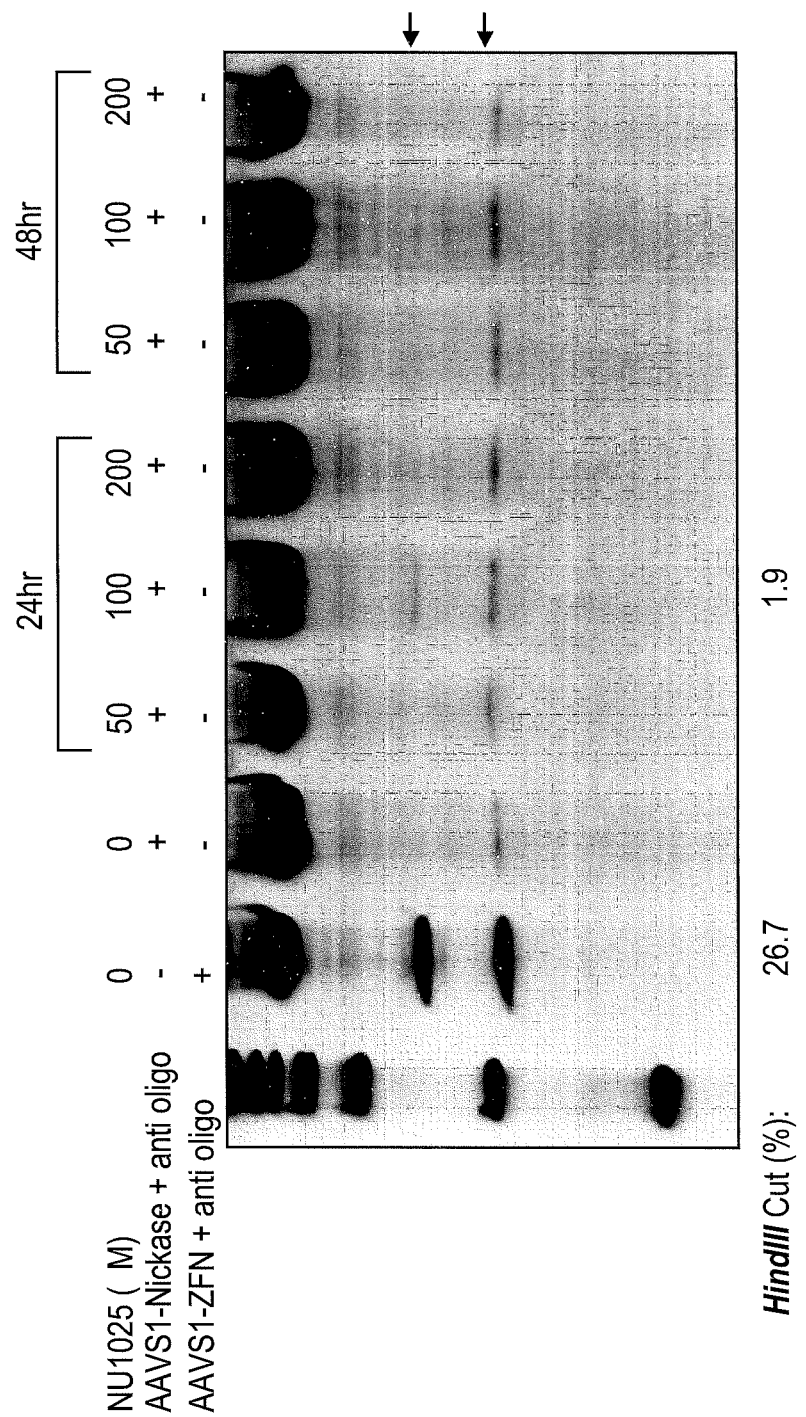
FIG. 7C shows targeted integration into the AAVS1 locus with an oligo in K562 cells using the PARP1 inhibitor NU1025.

In another experiment, K562 cells were treated with the PARP1 inhibitor NU1025. Briefly, two million K562 cells were nucleofected with 5 µg of double-stranded cleaving or nickase ZFNs specific for AAVS1 (U.S. Pat. No. 8,110,379)

with or without 3 µl of an antisense AAVS1 oligo (100 µM). The cells were immediately treated with PARP inhibitor NU1025 after nucleofection for 24 hr or 48 hr. All cells were harvested 48 hr after nucleofection. 1.0 µg of PCR DNA was subjected to HindIII digestion. As shown in FIG. 7C, detectable integration was observed with both the double-stranded cleaving or nickase ZFNs.

These results demonstrate that nickase nucleases can be used with DNA repair inhibitors to carry out targeted integration with high specificity.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method for targeted genomic disruption via microhomology-mediated end joining (MMEJ) in a cell, the method comprising:
    administering at least one nuclease to the cell, wherein the nuclease cleaves endogenous genomic sequences in the cell, wherein the nuclease is a zinc finger nuclease, a TALE effector domain nuclease (TALEN) and/or a CRISPR/Cas nuclease system; and
    growing the cell in a medium comprising at least one small molecule inhibitor of a DNA-dependent-protein kinase catalytic subunit (DNA-PKcs) protein and a small molecule inhibitor of a Poly-(ADP-ribose) polymerase 1/2 (PARP1/2) protein at 0.5 to 25 wherein the small molecule inhibitor is a nicotinamide; a isoquinolinone and a dihydroisoquinolinones; a benzimidazole; an indole; phthalazin-1(2H)-one; a quinazolinone; an isoindolinone and analogues and derivatives thereof; a phenanthridine; a phenanthridinone; a benzopyrone and analogues and derivatives thereof; an unsaturated hydroximic acid derivative and analogues and derivatives thereof; a pyridazine; caffeine, theophylline; thymidine and/or NU7026 and/or NU7441, wherein the endogenous genomic sequences in the cell are disrupted via MMEJ after cleavage by the at least one nuclease.

2. The method of claim 1, wherein the DNA-PKcs protein and/or (PARP1/2) protein is selected from the group consisting of PARP1, Ku70/80, DNA-PKcs, XRCC4/XLF, Ligase IV, Ligase III, XRCC1, Artemis Polynucleotide Kinase (PNK) and combinations thereof.

3. The method of claim 1, wherein the targeted genomic disruption comprises a deletion.

4. The method of claim 1, wherein the targeted genomic disruption comprises an insertion.

5. The method of claim 4, further comprising administering an exogenous sequence to the cell, wherein the exogenous sequence is integrated into the genome via homology directed repair (HDR) mechanisms following cleavage by the nuclease.

6. The method of claim 5, wherein the exogenous sequence is selected from the group consisting of a sequence encoding a protein, a regulatory sequence, a sequence that encodes a structural RNA and combinations thereof.

7. The method of claim 1, wherein the nuclease is administered using an expression vector or as mRNA.

8. The method of claim 1, wherein the cell further comprises a Rad52 mRNA.

* * * * *